(12) United States Patent
Maggio et al.

(10) Patent No.: US 8,415,405 B2
(45) Date of Patent: Apr. 9, 2013

(54) SILICONE (METH)ACRYLAMIDE MONOMER, POLYMER, OPHTHALMIC LENS, AND CONTACT LENS

(75) Inventors: Thomas L. Maggio, Jacksonville, FL (US); Michelle Carman Turnage, Jacksonville, FL (US); Michael R. Clark, Jacksonville, FL (US); Kazuhiko Fujisawa, Shiga (JP); Masataka Nakamura, Shiga (JP)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 0 days.

(21) Appl. No.: 13/048,469

(22) Filed: Mar. 15, 2011

(65) Prior Publication Data

US 2011/0237766 A1    Sep. 29, 2011

(30) Foreign Application Priority Data

Mar. 18, 2010    (JP) ................. 2010-061991

(51) Int. Cl.
*C08F 290/06* (2006.01)
*C07F 7/10* (2006.01)

(52) U.S. Cl. ........................ 523/107; 556/419

(58) Field of Classification Search .................. None
See application file for complete search history.

(56) References Cited

U.S. PATENT DOCUMENTS

| | | | |
|---|---|---|---|
| 4,711,943 A | 12/1987 | Harvey, III | |
| 4,834,753 A | 5/1989 | Sulc | |
| 4,890,911 A | 1/1990 | Sulc | |
| 5,336,797 A * | 8/1994 | McGee et al. | 556/419 |
| 5,399,737 A | 3/1995 | Park | |
| 5,505,884 A * | 4/1996 | Burke et al. | 264/1.1 |
| 5,512,205 A * | 4/1996 | Lai | 252/182.14 |
| 5,994,488 A | 11/1999 | Yokota | |
| 5,998,498 A * | 12/1999 | Vanderlaan et al. | 523/107 |
| 6,020,445 A | 2/2000 | Vanderlaan | |
| 6,367,929 B1 | 4/2002 | Maiden | |
| 7,214,809 B2 | 5/2007 | Zanini | |
| 7,396,890 B2 | 7/2008 | Zanini | |
| 2004/0192872 A1 * | 9/2004 | Iwata et al. | 528/25 |
| 2005/0176911 A1 | 8/2005 | Zanini | |
| 2006/0072069 A1 | 4/2006 | Laredo | |
| 2006/0165934 A1 | 7/2006 | Okazaki | |
| 2006/0276608 A1 * | 12/2006 | Lang et al. | 528/25 |
| 2007/0167592 A1 * | 7/2007 | Zanini et al. | 526/279 |
| 2008/0045612 A1 | 2/2008 | Rathore | |
| 2008/0231798 A1 * | 9/2008 | Zhou et al. | 351/160 H |
| 2008/0305292 A1 | 12/2008 | Okazaki | |
| 2010/0258961 A1 * | 10/2010 | Chang et al. | 264/1.38 |
| 2011/0133350 A1 * | 6/2011 | Qiu et al. | 264/1.1 |
| 2011/0211158 A1 * | 9/2011 | Iwata et al. | 351/160 H |

FOREIGN PATENT DOCUMENTS

| | | |
|---|---|---|
| EP | 1956033 B1 | 5/2009 |
| JP | 10212355 A | 8/1998 |
| WO | WO 2005078482 A1 | 8/2005 |
| WO | WO 2008005229 A2 | 1/2008 |
| WO | WO 2008005229 A3 | 1/2008 |
| WO | WO 2011005937 A2 | 1/2011 |
| WO | WO 2011005937 A3 | 1/2011 |

OTHER PUBLICATIONS

PCT International Search Report dated Oct. 13, 2011, for PCT Int'l. appln. No. PCT/US2011/028847.
PCT International Search Report, dated Jun. 27, 2011, for PCT Int'l Appln. No. PCT/2011/028842.
Andre Laschewsky et al., Macromol. Chem. Phys. 2001, vol. 202, pp. 276-286.
Volume III, Photoinitiators for Free Radical Cationic & Anionic Photopolymerization, 2$^{nd}$ Edition by J.V. Crivello & K. Dietliker; edited by G. Bradley; John Wiley and Sons; New York; 1998.

* cited by examiner

*Primary Examiner* — Robert S Loewe
(74) *Attorney, Agent, or Firm* — Karen A. Harding

(57) ABSTRACT

The present invention relates to a silicone (meth)acrylamide monomer, and this silicone (meth)acrylamide monomer is particularly suitable for use in contact lenses, intraocular lenses, artificial cornea, and the like.

18 Claims, 1 Drawing Sheet

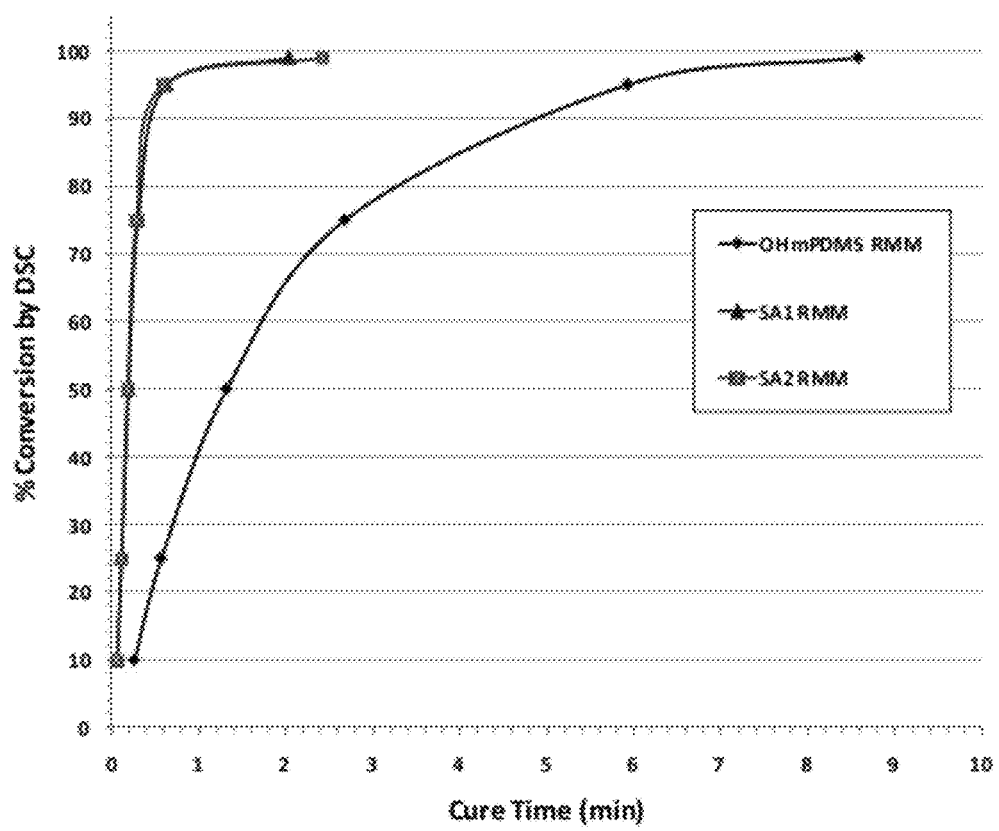

SILICONE (METH)ACRYLAMIDE MONOMER, POLYMER, OPHTHALMIC LENS, AND CONTACT LENS

RELATED APPLICATIONS

This application claims priority to Japanese Patent Application No.: JP-2010-061991 filed Mar. 18, 2010.

BACKGROUND OF THE INVENTION

The present invention relates to a silicone (meth)acrylamide monomer with a straight chain siloxanyl group and preferably with a hydroxyl group in a molecule. A polymer obtained by polymerizing this monomer is suitable for use in various medical implements such as ophthalmic lenses, endoscopes, catheters, transfusion tubes, gas transport tubes, stents, sheaths, cuffs, tube connectors, access ports, drainage bags, blood circuits, wound covering material, and various types of medicine carriers, but is particularly suitable for contact lenses, ophthalmic lenses, and artificial corneas.

DESCRIPTION OF THE RELATED ART

In recent years, silicone hydrogels obtained by copolymerizing a silicone monomer, a hydrophilic monomer, and a cross-linking agent monomer have become known as materials for contact lenses that are used for continuous wear. Patent document 1 discloses silicone acrylamide monomers expressed by the following formulas (x1) and (x2) as suitable for use in making silicone hydrogels.

[FORMULA 1]

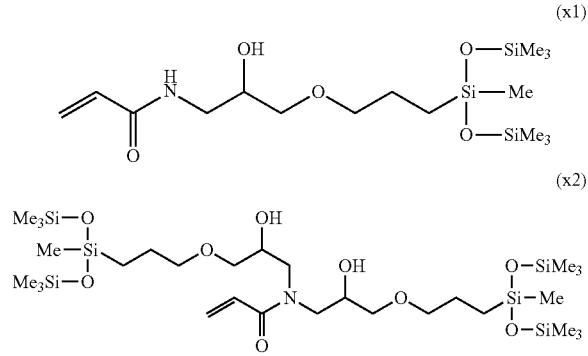

However, the silicone region of the silicone acrylamide monomer shown in patent document 1 is a branched siloxanyl group, so polymers obtained by polymerizing these monomers may have inferior shape recovery properties. Herein, branched refers to a condition where the Si—(O—Si)$_x$ bond (where x is an integer 1 or higher) beginning at the silicon atom that is bonded to the carbon backbone of the molecule is not a continuous single strand. Therefore, if a straight chain siloxanyl group is used, hydrophobicity will be increased and there is a concern that compatibility with hydrophilic substances will be inferior.

Furthermore, the composition of patent document 1 contains approximately from 30 to 40 weight parts of methacrylate ester. While the acrylamide monomer has a higher polymerization rate constant than the methacrylate ester during homopolymerization, the rate of acrylamide and methacrylate copolymerization is significantly lower and as a result the polymerization rate of the entire system will be reduced.

On the other hand, patent document 2 discloses a silicone acrylamide monomer expressed by the following formulae (y1) and (y2), and a silicone hydrogel made from this monomer and a hydrophilic acrylamide monomer.

[FORMULA 2]

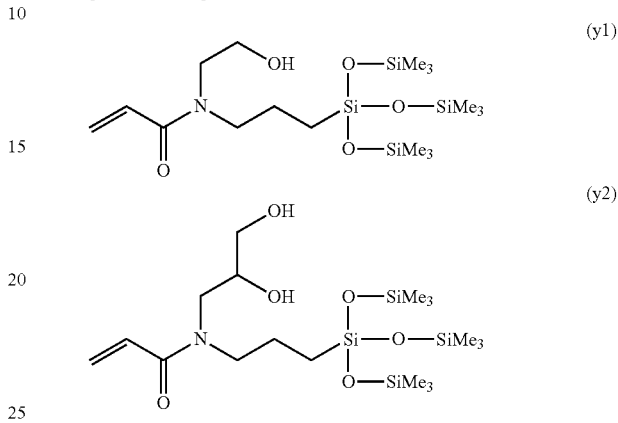

Acrylamide monomers account for the majority of the composition that is used in the silicone acrylamide monomer disclosed in patent document 2, and a higher polymerization rate for the entire system is anticipated. However, the silicone region of these monomers also has a branched siloxanyl group, so polymers obtained by polymerizing these monomers display inferior shape recovery. Furthermore, the amido bond of the acrylamide group has high hydrophilicity, and therefore providing a transparent lens may be difficult from the perspective of achieving both a sufficient amount of silicone component to provide high oxygen permeability and providing sufficient water content to provide flexibility to the lens. In particular, achieving a transparent lens is especially difficult if an internal wetting agent is added in order to increase the wettability of the surface.

References of Related Art

Patent Documents

Patent Document 1 US2005/0176911

Patent Document 2 Japanese Unexamined Patent Application H10-212355

SUMMARY OF THE INVENTION

The present invention relates to silicone (meth)acrylamide monomers with a fast polymerization rate, and a polymer obtained thereby having favorable transparency and shape recovery.

The present invention further relates to the following compositions. Namely, (1) A silicone (meth)acrylamide monomer comprising a (meth)acrylamide group and a straight chain siloxanyl group having two or more —OSi repeating units in a molecule.

(2) The silicone (meth)acrylamide monomer according to (1), wherein the silicone (meth)acrylamide monomer further comprises at least one hydroxyl group.

(3) The silicone (meth)acrylamide monomer according to (2), expressed by the following general formula (a).

[FORMULA 1]

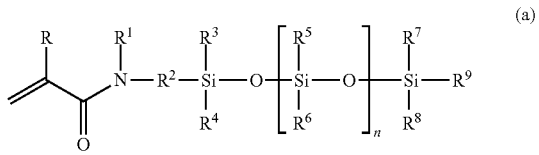

(R represents a hydrogen atom or a methyl group; $R^1$ represents a hydrogen atom or an alkyl or an aryl group with between 1 and 20 carbon atoms which may be substituted with hydroxyl, acid, ester, ether, thiol and combinations thereof; $R^2$ represents a $C_{1-10}$ alkylene group or arylene group that may be substituted with hydroxyl acid, ester, ether, thiol and combinations thereof; wherein at least one of either $R^1$ or $R^2$ has a hydroxyl group; $R^3$ to $R^9$ independently represent a $C_{1-20}$ alkyl group or an aryl group with between 1 and 20 carbon atoms, either of which may be substituted with fluorine, hydroxyl, acid, ester, ether, thiol and combinations thereof, and n is an integer in a range from 1 to 10.

The present invention further relates to polymers, ophthalmic lenses and contact lenses obtained by polymerizing a monomer mixture comprising at least one silicone (meth)acrylamide monomer as described herein.

DETAILED DESCRIPTION OF THE INVENTION

The present invention contains the silicone (meth)acrylamide monomer of the present invention and therefore can provide a silicone hydrogel with a high acrylamide monomer content, that is transparent, and that has an excellent balance between water content and wettability. The polymer obtained by polymerizing this silicone hydrogel is suitably used for various types of medical implements, particularly for ophthalmic lenses such as contact lenses, intraocular lenses, and artificial cornea, and especially for contact lenses.

A silicone (meth)acrylamide monomer of the present invention has a (meth)acrylamide group and a straight chain siloxanyl group in a molecule, and preferably has at least one hydroxyl group in a molecule. A siloxanyl group refers to a group having at least one Si—O—Si bond, "straight chain" refers to a structure where a bond is formed in a single line beginning with a silicon atom that is bonded to an alkyl group which has a (meth)acrylamide group, or in other words a silicone (meth)acrylamide monomer having a straight chain siloxanyl group refers to a structure expressed by the following general formula (p)

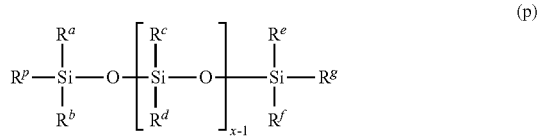

In formula (p), $R^p$ represents an alkyl group with a (meth)acrylamide group. $R^a$ through $R^g$ represent groups that do not contain a silicon atom. x represents an integer 2 or higher. Unlike the silicone (meth)acrylamides of the present invention, silicone (meth)acrylamides of the prior art contained at least a portion of the silicone in a pendant chain. In formula (p), x represents an integer 2 or higher, and if x is too small, sufficient oxygen permeability will not be achieved, but if too large, compatibility with the hydrophilic monomer will decrease, and achieving a transparent lens will be more difficult. Therefore, in some embodiments, x is a value between 3 and 7, between 3 and 6, and between 3 and 5. Furthermore, preferably x does not have a distribution in order to increase a reproducibility of the physical properties of the polymer obtained. For the present invention, the phrase "does not have a distribution" indicates a condition wherein various peaks for different values of x, a ratio of the largest peak is 80% or higher, as measured by GC for the case of a monomer that can be measured using gas chromatography (GC) (FID analyzer), or as measured by liquid chromatography (LC) (RI analyzer) for the case of a monomer has such high boiling point that cannot be measured using GC.

Furthermore, in this specification, (meth)acryl refers to acryl and methacryl and (meth)acrylamide refers to acrylamide and methacrylamide.

The silicone (meth)acrylamide monomer of the present invention without hydroxyl group includes the monomer expressed by the following formulae (s1), (s5) and (s6);

[FORMULA]

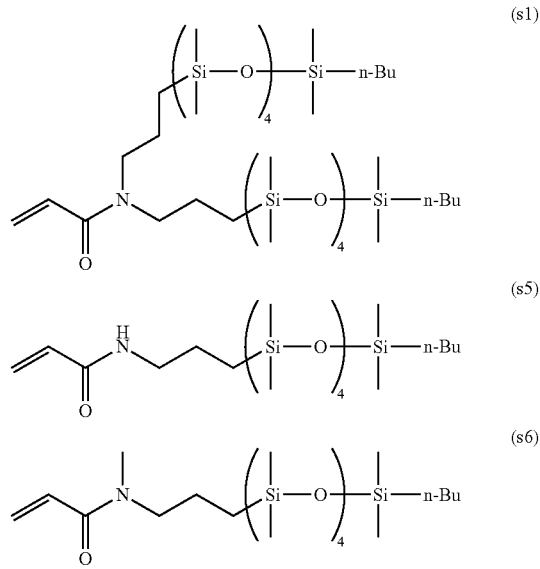

Of these monomers, the monomers expressed by the formulae (s5) and (s6) are more preferable from the perspective of low modulus of the silicone hydrogel obtained.

With the present invention, there is concern that a hydrophobicity will increase and a compatibility with hydrophilic substances will be inferior if the monomer contains a straight chain siloxanyl group, but a hydrophilicity can be increased by having an amido bond and a hydroxyl group. However, if a number of hydroxyl groups is too high, an elastic modulus of the polymer will be undesirably high and therefore the number of hydroxyl groups per monomer unit is in one embodiment between 1 and 6, and in another between 1 and 3, further 1 or 2, and, where wettability (low contact angles) of the polymer obtained is particularly important, 2.

Furthermore, if a branched siloxanyl group is present in addition to the straight chain siloxanyl group, the hydrophobicity may be undesirably high. Therefore, in one embodiment a branched siloxanyl group is present in an amount less than about 15 weight % based upon the polymerization components, and in other embodiments a branched siloxanyl group is not present.

The silicone (meth)acrylamide monomer of the present invention has a (meth)acrylamide group as a polymeric group in order to increase a polymerization rate, and therefore an increased polymerization rate can be anticipated. When an acrylamide monomer is used as a hydrophilic substance, this effect is particularly prominent. This increase in polymerization rate decreases the cure time needed to complete the polymerization and yield the final material. Of acrylamide groups and methacrylamide groups, acrylamide groups are preferable from a perspective of further increasing the polymerization rate. As described above, ensuring transparency is difficult if an amide group is present, but if a hydroxyl group is present, a drop in the transparency due to the presence of an amide group can be prevented. The details are unclear, but it is thought that in addition to acting as a compatibilizer, the hydroxyl group also acts to increase wettability.

An example of a preferable structure of the silicone (meth) acrylamide monomer of the present invention with at least one hydroxyl group is the monomer expressed by the following general formula (a).

[FORMULA 4]

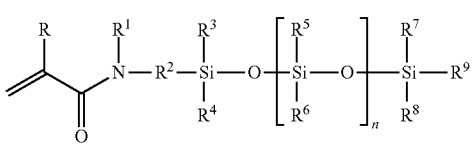

(a)

In formula (a), R represents a hydrogen atom or a methyl group. In one embodiment, R is a hydrogen atom and the silicone (meth)acrylamide displays an increased polymerization rate. In formula (a), $R^1$ represents a hydrogen atom or an alkyl or an aryl group with between 1 and 20 carbon atoms which may be substituted with hydroxyl, acid, ester, ether, thiol and combinations thereof.

In one embodiment, $R^1$ is a hydrogen atom or an alkyl having between 1 and 5 carbon atoms which may be substituted with hydroxyl, acid or ester groups. In another embodiment $R^1$ is an alkyl group having 1-5 carbon atoms, and may be unsubstituted or substituted with at least one hydroxyl group. Examples of $R^1$ include hydrogen atoms, methyl groups, ethyl groups, propyl groups, n-propyl groups, i-propyl groups, n-butyl groups, s-butyl groups, t-butyl groups, n-pentyl groups, i-pentyl groups, s-pentyl groups, neopentyl groups, hexyl groups, heptyl groups, octyl groups, nonyl groups, decyl groups, dodecyl groups, eicosyl groups, phenyl groups, naphthyl groups, all of which may be substituted as described above, and the like. In one embodiment, $R^1$ is selected from methyl groups, ethyl groups, n-propyl groups, i-propyl groups, n-butyl groups, s-butyl groups, or t-butyl groups, any of which may be hydroxyl substituted. In another embodiment $R^1$ is selected from hydrogen atoms, methyl groups, ethyl groups. Hydrogen atoms, methyl groups and ethyl groups provide the silicone (meth)acrylamide monomer with increased hydrophilicity. Examples of hydroxyl substituted $R^1$ groups include 2-hydroxyethyl groups, 2-hydroxypropyl groups, 3-hydroxypropyl groups, 2,3-dihydroxypropyl groups, 4-hydroxy butyl groups, 2-hydroxy-1,1-bis(hydroxymethyl)ethyl groups, 2-hydroxymethylphenyl groups, 3-hydroxymethylphenyl groups, 4-hydroxymethylphenyl groups, and the like. In one embodiment R' is selected from 2-hydroxyethyl groups, 2-hydroxypropyl groups and 2,3-dihydroxypropyl groups, and in another embodiment $R^1$ is a 2,3-dihydroxypropyl groups. 2,3-dihydroxypropyl groups provide the silicone (meth)acrylamide with increased hydrophilicity. Furthermore, if the transparency of the polymer obtained by polymerizing the silicon (meth)acrylamide monomer must be further enhanced, R' is preferably not a hydrogen atom.

$R^2$ represents a bivalent $C_{1-10}$ alkylene group or aryl group that may be substituted with hydroxyl, acid, ester, ether, thiol and combinations thereof. In another embodiment $R^2$ is selected from $C_{1-5}$ alkylene groups, which may be unsubstituted or substituted with hydroxyl, ether groups and combinations thereof. In another embodiment $R^2$ is selected from $C_{2-5}$ alkylene groups, which may be unsubstituted or substituted with hydroxyl, ether groups and combinations thereof, and in yet another embodiment, $R^2$ is a $C_3$ alkylene groups, which may be unsubstituted or substituted with hydroxyl, ether groups and combinations thereof. In yet another embodiment $R^2$ is a group of formula (d):

Or the groups expressed by the following formula (b):

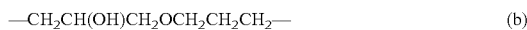

Examples of suitable $R^2$ groups include methylene groups, ethylene groups, propylene groups, butylene groups, pentalene groups, octalene groups, decylene groups, and phenylene groups, any of which may be unsubstituted or substituted with at least one hydroxyl and, a group represented by the following formula (d):

and the groups expressed by the following formula (b):

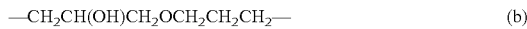

These alkylene and arylene groups can be straight or branched. Of these, ethylene, propylene, butylene, the groups expressed by formulae (d), and (b) are preferable in some embodiments and silicone (meth)acrylamides containing them polymerize to form a polymer with low elastic modulus. In another embodiment $R^2$ is selected from an ethylene group, propylene group, or butylene group, and in another embodiment, $R^2$ is n-propylene group, from a perspective of achieving a balance between hydrophobicity and a lowered elastic modulus for the polymer obtained by polymerizing the silicone (meth)acrylamide monomer.

In formula (a), $R^3$ through $R^9$ independently represent an alkyl group or an aryl group with between 1 and 20 carbon atoms either of which may be substituted with fluorine, hydroxyl, acid, ester, ether, thiol and combinations thereof. Examples of $R^3$ through $R^8$ include hydrogen atoms, methyl groups, ethyl groups, propyl groups, n-propyl groups, i-propyl groups, n-butyl groups, s-butyl groups, t-butyl groups, n-pentyl groups, i-pentyl groups, s-pentyl groups, neopentyl groups, hexyl groups, heptyl groups, octyl groups, nonyl groups, decyl groups, dodecyl groups, eicosyl groups, phenyl groups, naphthyl groups, any of which may be substituted by fluorine, hydroxyl or combinations thereof and the like. In some embodiments, an alkyl group with between 1 and 4 carbon atoms is preferable, and a methyl group is most preferable, from a perspective of increasing the oxygen permeability. $R^9$ independently represents an alkyl group or an aryl group with between 1 and 20 carbon atoms. Examples of $R^9$ include hydrogen atoms, methyl groups, ethyl groups, propyl groups, n-propyl groups, i-propyl groups, n-butyl groups, s-butyl groups, t-butyl groups, n-pentyl groups, i-pentyl groups, s-pentyl groups, neopentyl groups, hexyl groups, heptyl groups, octyl groups, nonyl groups, decyl groups, dodecyl groups, eicosyl groups, phenyl groups, naphthyl groups, any of which may be substituted by fluorine, hydroxyl or combinations thereof and the like. With regards to $R^9$, an alkyl group with between 1 and 4 carbon atoms is preferable, and in some embodiments, an n-butyl group, s-butyl group, or a t-butyl group, which may be unsubstituted or hydroxyl substituted are most preferable, based on a balance between the oxygen permeability and a hydrolysis resistance of the siloxanyl group. In other embodiments $R^9$ may be methyl or ethyl.

In formula (a), n represents an integer between 1 and 10, and if n is too small, desirable oxygen permeability may not be achieved, but if too large, compatibility with the hydrophilic monomer will decrease, and achieving a transparent lens will be more difficult. Therefore in some embodiments n is a value between 2 and 6, between 2 and 5, and between 2 and 4. Any of the lower limit values and any of the preferred upper limit values can be combined together. Furthermore, preferably n does not have a distribution in order to increase a reproducibility of the physical properties of the polymer obtained. For the present invention, the phrase "does not have a distribution" indicates a condition wherein various peaks for different values of n, a ratio of the largest peak is 80% or higher, as measured by GC for the case of a monomer that can be measured using gas chromatography (GC) (FID analyzer), or as measured by liquid chromatography (LC) (RI analyzer) for the case of a monomer has such high boiling point that cannot be measured using GC.

The silicone (meth)acrylamide monomers of the present invention can be prepared by any method known to those of skill in the art of synthetic organic chemistry. An example of preparation method for silicone (meth)acrylamide monomer expressed by the formula (a)

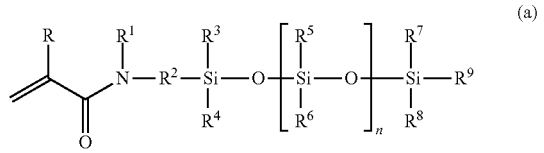

(a)

comprises hydrosilylation of the compound expressed by the following formula (a10)

(a10)

with a linear siloxane expressed by the following formula (a11)

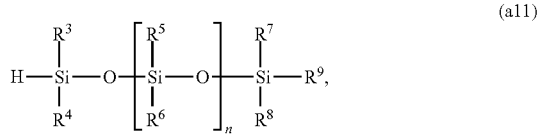

(a11)

and comprises (meth)acrylation of the compound expressed by the following formula (a12)

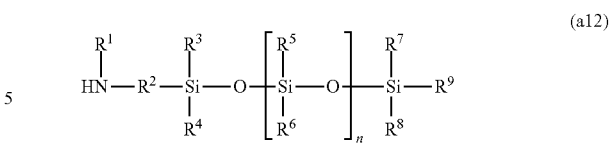

(a12)

obtained from the hydrosilylation. In the formula (a10), $Q^1$ comprise a carbon-carbon double bond and is converted to $R^2$ of the formula (a) by hydrosilylation.

One of more specific example of preparation method for a silicone (meth)acrylamide monomer of the present invention is a method for the monomers expressed by the following formula (a20).

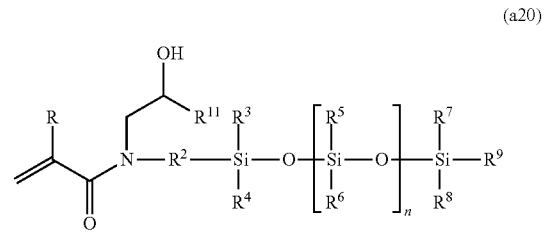

(a20)

The preparation method comprises ring-opening reaction of epoxide by amine, protection of hydroxyl group(s), hydrosilylation, acrylation, and de-protection of hydroxyl group(s). In the formula (a20), R, $R^2$, $R^3$ through $R^9$, and n are the same with those in the formula (a) above, and —$CH_2CH(OH)R^{11}$ in the formula (a20) represents $R^1$ in the formula (a).

In the ring-opening reaction of epoxide by amine at the first step, a compound expressed by the formula (a23) can be obtained by reacting an epoxide expressed by the following formula (a21) with an amine expressed by the following formula (a22).

(a21)

(a22)

(a23)

In the formulae (a22) and (a23), $Q^2$ comprises a carbon-carbon double bond and is converted to $R^2$ in the formula (a20) by hydrosilylation of the double bond.

The (a22)/(a21) ratio of the reaction is preferably from about 1 to about 50, more preferably from about 1.5 to about 30, and most preferably from about 2 to about 15 to reduce di-substituted and tri-substituted amine by-product. The temperature of the reaction is preferably from about −20° C. to about 100° C., more preferably from about 0° C. to about 50° C., and most preferably from about 20° C. to about 40° C. to avoid vaporization of amines. The time of the reaction is from about 1 hour to about 72 hours.

In the second step, hydroxyl group(s) of the compound (a23) from the first step may be protected to avoid side-reaction of hydrosilylation. One suitable example of protecting groups is trimethylsilyl group, which can protect and de-protect in mild condition. Any known reagents for trimethylsilylation of hydroxyl group can be used, such as trimethylsilyl chloride, trimethylsilyl trifluoromethanesulfonate, N-Methyl-N-trimethylsilylacetamide, and hexamethyldisilazane. Among these, hexamethyldisilazane is preferable because no salt remains after reaction. The temperature of the trimethylsilylation reaction with hexamethyldisilazane is from about 40° C. to about 150° C., more preferably from about 50° C. to about 130° C., and most preferably from about 70° C. to 120° C., and the time of the reaction is from about 0.5 hour to about 5 hours. Purification by vacuum distillation is preferable before the next step.

In the third step, the compound expressed by the following formula (a24),

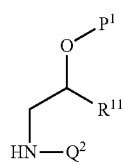

(a24)

wherein $P^1$ represents a protecting group, from the second step is reacted with linear siloxane expressed by the following formula (a25).

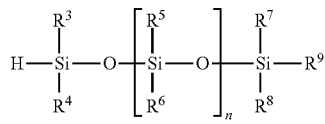

(a25)

wherein $R^3$ through $R^9$, and n are the same in the formula (a). The ratio of (a25)/(a24) is between about 0.5 and about 2.0, more preferably between about 0.8 and about 1.2, and most preferably between 0.9 and 1.1. Suitable catalysts include platinum (0) 2,4,6,8-tetramethyl-2,4,6,8-tetravinylcyclotetrasiloxane, platinum (0) 1,3-dimethyl-1,3-divinyldisiloxane, hydrogen hexachloroplatinate (IV), and more preferably platinum (0) 2,4,6,8-tetramethyl-2,4,6,8-tetravinylcyclotetrasiloxane, platinum (0) 1,3-dimethyl-1,3-divinyldisiloxane. The catalyst is used in an amount between about 1 ppm and about 10000 ppm, more preferably between about 5 ppm and about 5000 ppm, and most preferably between about 10 ppm and about 1000 ppm. The temperature of the reaction is preferably between about −20° C. to about 180° C., more preferably between about −10° C. to about 150° C., and most preferably between about 0° C. to about 130° C.

In the fourth step, the amino group of the compound expressed by the following formula (a26)

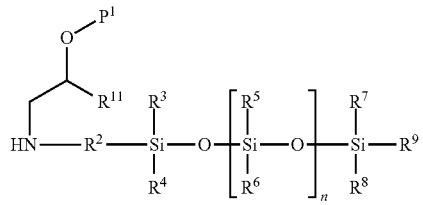

(a26)

from the third step can be reacted with an acrylating agent, such as (meth)acryloyl halide, (meth)acrylic anhydride. When (meth)acryloyl halide is used, the temperature of the reaction is preferably between about −80° C. to about 40° C., more preferably between about −40° C. to about 30° C., and most preferably between about −20° C. to about 10° C. Inhibitor may be added in an amount between 1 ppm and 5000 ppm, more preferably between 10 ppm and 1000 ppm, most preferably 50 ppm and 500 ppm to avoid polymerization during monomer synthesis. Suitable inhibitors include hydroquinone monomethylether, butylated hydroxytoluene, mixture thereof and the like. As a result of this step, a monomer expressed by the following formula (a27)

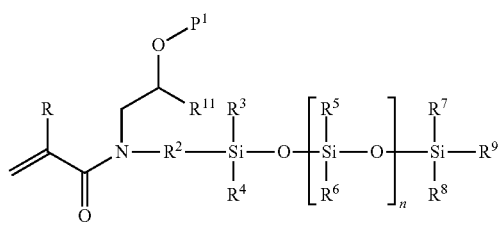

(a27)

is obtained. The monomer (a27) is preferable from the perspective of compatibility with wide range of hydrophobic and hydrophilic co-monomers. The monomer (a27) can be de-protected after polymerization, thereby both desirable compatibility in monomer mixture and desirable transparency of polymer derived from hydroxyl groups can be achieved.

In the fifth step, hydroxyl group(s) of the compound expressed by the formula (a27) is de-protected. The method and condition of de-protection depends on $P^1$. If $P^1$ is trimethylsilyl group, de-protection with acetic acid in methanol is preferable from the perspective of the mild reaction condition. The temperature of the reaction is preferably between about 20° C. to about 40° C., and the time of the reaction is preferably between about 0.5 hour to about 3 hours. After de-protection, the obtained silicone (meth)acrylamide monomer can be purified by various method including column chromatography, vacuum distillation, molecular distillation, treatment with ion-exchange resin, and the combination thereof. As a result of this step, silicone (meth)acrylamide monomer expressed by the formula (a20) is obtained.

Another more specific example of preparation method for a silicone (meth)acrylamide monomer of the present invention is a method for the monomers expressed by the following formula (a30)

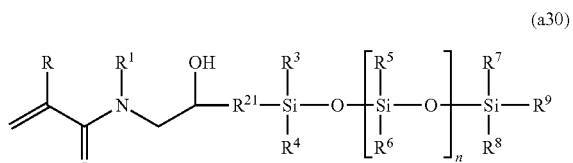

(a30)

The preparation method comprises ring-opening reaction of epoxide by amine, protection of hydroxyl group(s), hydrosilylation, acrylation, and de-protection of hydroxyl group(s). In the formula (a30), R, $R^1$, $R^3$ through $R^9$, and n are the same with those in the formula (a) above, and —CH$_2$CH(OH) $R^{21}$— in the formula (a30) represents $R^1$ in the formula (a).

In the ring-opening reaction of epoxide by amine at the first step, a compound expressed by the formula (a33) can be obtained by reacting an epoxide expressed by the following formula (a31) with an amine expressed by the following formula (a32).

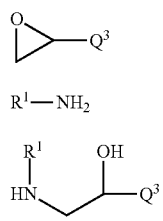

(a31)

$R^1-NH_2$ (a32)

(a33)

In the formulae (a31) and (a33), $Q^3$ comprises a carbon-carbon double bond and is converted to $R^2$ in the formula (a30) by hydrosilylation of the double bond.

The (a32)/(a31) ratio of the reaction is preferably from about 1 to about 50, more preferably from about 1.5 to about 30, and most preferably from about 2 to about 15 to reduce di-substituted and tri-substituted amine by-product. The temperature of the reaction is preferably from about −20° C. to about 100° C., more preferably from about 0° C. to about 50° C., and most preferably from about 20° C. to about 40° C. to avoid vaporization of amines. The time of the reaction is from about 1 hour to about 72 hours.

In the second step, hydroxyl group(s) of the compound (a33) from the first step may be protected to avoid side-reaction of hydrosilylation. One suitable example of protecting groups is trimethylsilyl group, which can protect and de-protect in mild condition. Any known reagents for trimethylsilylation of hydroxyl group can be used, such as trimethylsilyl chloride, trimethylsilyl trifluoromethanesulfonate, N-Methyl-N-trimethylsilylacetamide, and hexamethyldisilazane. Among these, hexamethyldisilazane is preferable because no salt remains after reaction. The temperature of the trimethylsilylation reaction with hexamethyldisilazane is from about 40° C. to about 150° C., more preferably from about 50° C. to about 130° C., and most preferably from about 70° C. to 120° C., and the time of the reaction is from about 0.5 hour to about 5 hours. Purification by vacuum distillation is preferable before the next step.

In the third step, the compound expressed by the following formula (a24),

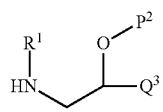

(a34)

wherein $P^2$ represents a protecting group, from the second step is reacted with linear siloxane expressed by the following formula (a35).

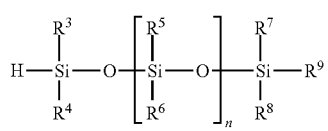

(a35)

wherein $R^3$ through $R^9$, and n are the same in the formula (a). The ratio of (a35)/(a34) is between about 0.5 and about 2.0, more preferably between about 0.8 and about 1.2, and most preferably between 0.9 and 1.1. Suitable catalysts include platinum (0) 2,4,6,8-tetramethyl-2,4,6,8-tetravinylcyclotetrasiloxane, platinum (0) 1,3-dimethyl-1,3-divinyldisiloxane, hydrogen hexachloroplatinate (IV), and more preferably platinum (0) 2,4,6,8-tetramethyl-2,4,6,8-tetravinylcyclotetrasiloxane, platinum (0) 1,3-dimethyl-1,3-divinyldisiloxane. The catalyst is used in an amount between about 1 ppm and about 10000 ppm, more preferably between about 5 ppm and about 5000 ppm, and most preferably between about 10 ppm and about 1000 ppm. The temperature of the reaction is preferably between about −20° C. to about 180° C., more preferably between about −10° C. to about 150° C., and most preferably between about 0° C. to about 130° C.

In the fourth step, the amino group of the compound expressed by the following formula (a36)

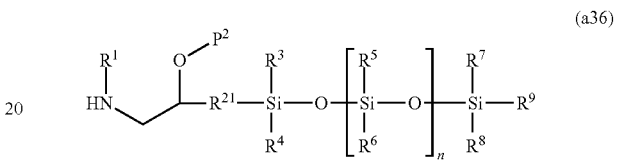

(a36)

from the third step can be reacted with an acrylating agent, such as (meth)acryloyl halide, (meth)acrylic anhydride. When (meth)acryloyl halide is used, the temperature of the reaction is preferably between about −80° C. to about 40° C., more preferably between about −40° C. to about 30° C., and most preferably between about −20° C. to about 10° C. Inhibitor may be added in an amount between 1 ppm and 5000 ppm, more preferably between 10 ppm and 1000 ppm, most preferably 50 ppm and 500 ppm to avoid polymerization during monomer synthesis. Suitable inhibitors include hydroquinone monomethylether, butylated hydroxytoluene, mixture thereof and the like. As a result of this step, a monomer expressed by the following formula (a37)

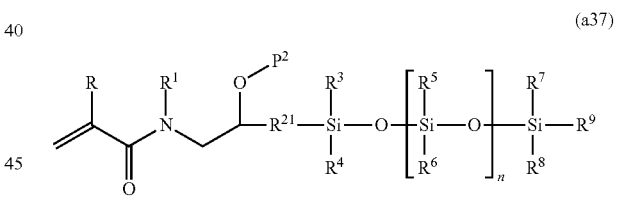

(a37)

is obtained. The monomer expressed by the formula (a37) is preferable from the perspective of compatibility with wide range of hydrophobic and hydrophilic co-monomers. The monomer (a37) can be de-protected after polymerization, thereby both desirable compatibility in monomer mixture and desirable transparency of polymer derived from hydroxyl groups can be achieved.

In the fifth step, hydroxyl group(s) of the compound expressed by the formula (a37) is de-protected. The method and condition of de-protection depends on $P^2$. If $P^2$ is trimethylsilyl group, de-protection with acetic acid in methanol is preferable from the perspective of the mild reaction condition. The temperature of the reaction is preferably between about 20° C. to about 40° C., and the time of the reaction is preferably between about 0.5 hour to about 3 hours. After de-protection, the obtained silicone (meth)acrylamide monomer can be purified by various method including column chromatography, vacuum distillation, molecular distillation, treatment with ion-exchange resin, and the combination thereof. As a result of this step, silicone (meth)acrylamide monomer expressed by the formula (a30) is obtained.

The polymer of the present invention is obtained via polymerization of a base formulation containing silicone (meth) acrylamide monomer. If a range for the silicone (meth)acrylamide monomer contained is too low, the oxygen permeability of the polymer may be insufficient, but if the range is too high, the hydrophilicity may be insufficient, so the monomer and polymer components in the monomer mixture are between 30 and 98 weight %, in some embodiments between about 40 and about 80 weight %, and most in other embodiments between about 50 and about 70 weight %. Lower limit values include about 30 weight %, about 40 weight %, and about 50 weight %. Upper limit values include about 98 weight %, about 80 weight %, and about 70 weight %. Any of the preferred lower limit values and any of the preferred upper limit values can be combined together.

The polymer of the present invention is preferably obtained by copolymerizing at least one hydrophilic monomer with at least one silicone (meth)acrylamide monomer. Examples of the hydrophilic monomer include (meth)acrylate monomer such as 2-hydroxyethyl (meth)acrylate, 2-(2-hydroxyethoxy) ethyl (meth)acrylate, glyceryl (meth)acrylate, and poly(ethyleneglycol) mono(meth)acrylate, polymerizable carboxylic acid monomer such as (meth)acrylic acid, itaconic acid, crotonic acid, vinyl benzoic acid, N-vinylamide monomer such as N-vinylpyrrolidone, N-vinylformamide, N-vinylacetamide, and N-vinyl-N-methylacetamide, and (meth)acrylamide monomer such as (meth)acrylamide, N,N-dimethyl (meth)acrylamide, N,N-diethyl (meth)acrylamide, N-isopropyl (meth)acrylamide, (meth)acryloyl morpholine, N-methoxymethyl (meth) acrylamide, N-hydroxymethylacrylamide and the like. Among these hydrophilic monomers, (meth) acrylamide monomer is preferably used in some embodiments because the polymerization rate of the entire system will be increased and copolymerization properties with the silicone (meth)acrylamide monomer will be favorable. Of the (meth)acrylamide monomers, N,N-dimethylacrylamide is preferable from the perspective of the polymerization rate and the balance between hydrophobicity and compatibility with the silicone monomer.

If a range for the amount of hydrophilic monomer that is used is too high, the oxygen permeability may be reduced, but if too low, the silicone hydrogel may be too hard, and therefore the amount of hydrophilic monomer is between about 1 and about 50 weight %, in some embodiments between % 10 and 40 weight %, and other embodiments between about 15 and about 35 weight %, based on the monomer and polymer component in the monomer mixture. Lower limit values about 1 weight %, about 10 weight %, and about 15 weight %. Upper limit values include about 50 weight %, about 40 weight %, and about 35 weight %. Any of the preferred lower limit values and any of the preferred upper limit values can be combined together.

In one embodiment, the polymer of the present invention may use a hydrophilic (meth)acrylamide monomer with two or more hydroxyl groups in the molecule independently from the aforementioned hydrophilic monomer, or in addition to the aforementioned hydrophilic monomer. In particular, if the hydrophilic polymers described later are used, the transparency of the polymer may easily deteriorate, so a hydrophilic (meth)acrylamide monomer is preferably used. When included, the amount of the hydrophilic (meth)acrylamide monomer is between about 1 and about 50 weight %, more preferably between about 1 and about 30 weight %, and most preferably between about 1 and about 15 weight %, based on the monomer and polymer component in the monomer mixture. An example of a hydrophilic (meth)acrylamide monomer containing two or more hydroxyl groups in the molecule include the monomers expressed by the following general formulae (c1) through (c3).

[FORMULA 5]

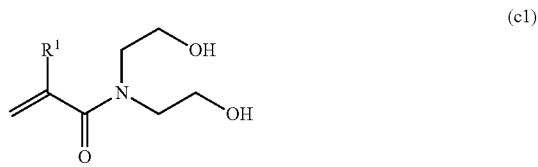
(c1)

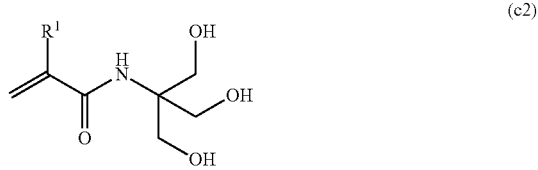
(c2)

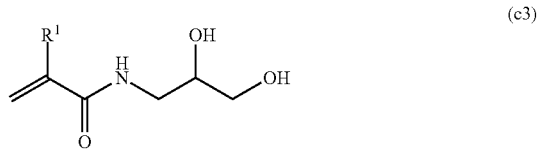
(c3)

In formulae (c1) through (c3), R' independently represents a hydrogen atom or a methyl group. In one embodiment, the hydrogen atoms are preferable from the perspective of increasing the polymerization rate. Furthermore, of these monomers, the monomers expressed by formula (c1) are preferable from a perspective of increasing the transparency of the polymer obtained.

In another embodiment, the polymer of the present invention may use a hydrophilic N-(mono-hydroxyl substituted $C_1$-$C_{20}$ alkyl)methacrylamide or N-(mono-hydroxyl substituted $C_6$-$C_{20}$ aryl)methacrylamide monomer independently from the aforementioned hydrophilic monomer. Preferably the polymer may use one of those monomers in addition to the aforementioned hydrophilic monomer. In one embodiment, if the hydrophilic polymers described later are used, the transparency of the polymer may easily deteriorate, so a hydrophilic methacrylamide monomer is used. The amount of the hydrophilic methacrylamide monomer is about between 1 and about 50 weight %, in one embodiment between about 1 and about 30 weight %, and in another embodiment between about 1 and about 15 weight %, based on the monomer and polymer component in the monomer mixture. An example of a hydrophilic methacrylamide monomer include N-hydroxymethylmethacrylamide, N-(2-hydroxyethyl)methacrylamide, N-(2-hydroxypropyl)methacrylamide, N-(3-hydroxypropyl)methacrylamide, N-(2-hydroxybutyl) methacrylamide, N-(3-hydroxybutyl)methacrylamide, N-(4-hydroxy butyl)methacrylamide, N-(2-hydroxymethylphenyl)methacrylamide, N-(3-hydroxymethylphenyl)methacrylamide, N-(4-hydroxymethylphenyl)methacrylamide and the like. These alkyl and aryl groups can be straight or branched. Of these, monomers, N-(2-hydroxyethyl)methacrylamide monomer is preferable from a perspective of increasing the transparency of the polymer obtained.

In one embodiment the monomer mixture for obtaining the polymer of the present invention additionally contains between about 1 and about 30% of a hydrophilic polymer with a molecular weight of about 1000 or higher in the monomer and polymer component of the monomer mixture in order to enhance wettability, resistance to adhesion of proteins, resistance to adhesion of lipids and combinations thereof.

Examples of hydrophilic polymers that are used in the polymer of the present invention include poly-N-vinyl pyrrolidone, poly-N-vinyl-2-piperidone, poly-N-vinyl-2-caprolactum, poly-N-vinyl-3-methyl-2-caprolactum, poly-N-vinyl-3-methyl-2-piperidone, poly-N-vinyl-4-methyl-2-piperidone, poly-N-vinyl-4-methyl-2-caprolactum, poly-N-vinyl-3-ethyl-2-pyrrolidone, poly-N-vinyl-4,5-dimethyl-2-pyrrolidone, polyvinyl imidazole, poly-N-vinyl formamide, poly-N-vinyl acetamide, poly-N-methyl-N-vinyl acetamide, poly-N,N-dimethyl acrylamide, poly-N,N-diethyl acrylamide, poly-N-isopropyl acrylamide, polyvinyl alcohol, polyacrylate, polyethylene oxide, poly-2-ethyl oxazoline, heparine, polysaccharide, poly-acryloyl morpholine, and mixtures and copolymers thereof. The hydrophilic polymers selected from, polyvinylpyrrolidone, poly-N,N-dimethyl acrylamide, polyacrylic acid, polyvinyl alcohol, and mixtures and copolymers thereof may be particularly effective at enhancing the wettability of certain silicone hydrogels. Polyvinylpyrrolidone and poly-N,N-dimethyl acrylamide provide a balance between the wet ability and the compatibility to the polymerization mix in certain formulations. Examples of suitable wetting agents are disclosed in US2006-0072069A1, U.S. Pat. No. 6,367,929 and US-2008-0045612A1.

If the amount of hydrophilic polymer that is used in the silicone hydrogel related to the present invention is too low, the desired wettability may not be achieved, but if too high, the hydrophilic polymer may not easily dissolve in the polymerization base liquid, and therefore the amount is between about 1 and about 30 weight %, between about 2 and about 25 weight %, and between about 3 and about 20 weight % of the monomer and polymer component in the polymerization mixture. Lower limit values include about 1 weight %, about 2 weight %, preferably about 3 weight %, and about 6 weight %. Upper limit values include about 30 weight %, about 25 weight %, about 20 weight %, about 9 weight %. Any of the lower limit values and any of the upper limit values can be combined together.

If a range of the molecular weight of the hydrophilic polymer that is used in the silicone hydrogel of the present invention is too low, desirable wettability may not be provided, but if too high, the solubility in the polymerization mixture may be inferior, and viscosity of the polymerization mixture will be increased. In one embodiment, the molecular weight is between about 1000 Daltons and about 10 million Daltons, in other embodiments between about 100,000 Daltons and about 1 million Daltons, and in other embodiments between about 200,000 Daltons and about 800,000 Daltons. In embodiments where the hydrophilic polymer comprises at least one reactive group capable of covalently bonding with the silicone hydrogel matrix, the molecular weight may be at least about 2000 Daltons, at least about 5,000 Daltons; and in some embodiments between about 5,000 to about 180,000 Daltons, or between about 5,000 Daltons to about 150,000 Daltons. Lower limit values include about 1000 Daltons, more about 100,000 Daltons, and about 200,000 Daltons. Upper limit values include about 10 million Daltons, about 1 million, and about 800,000 Daltons. Any of the preferred lower limit values and any of the preferred upper limit values can be combined together. The molecular weight of the hydrophilic polymer of the present invention is expressed by the weighted average molecular weight (Mw) measured by gel permeation chromatography (column: TSK gel GMP-WXL manufactured by Tosoh Corporation, mobility phase: water/methanol=50/50, 0.1 N lithium nitrate added, flow rate: 0.5 mL/minute, detector: differential refractive index detector, molecular weight standard sample: polyethylene glycol).

Of the monomer components used for polymerizing the polymer of the present invention, if the acrylamide monomer content is too low, the overall polymerization rate will be decreased, so the amount of all acrylamide monomers is in some embodiments about 90 weight % or higher, about 95 weight % or higher, and in some embodiments about 99 weight % or higher.

The polymer of the present invention can include a monomer with two or more reactive groups as a copolymerization component. In this case, the polymer of the present convention is made to be solvent resistant. Preferable examples of monomers with two or more polymeric groups include bifunctional and polyfunctional acrylates such as ethylene glycol (meth)acrylate, diethylene glycol di(meth)acrylate, triethylene glycol di(meth)acrylate, neopentyl glycol di(meth)acrylate, tetraethylene glycol di(meth)acrylate, glyceryl tri(meth)acrylate, pentaerythritol tetra(meth)acrylate, and trimethylol propane tri (meth)acrylate, and bisacrylamides such as N,N'-methylene bisacrylamide, N,N'-ethylene bisacrylamide, N,N'-propylene bisacrylamide, and the like. Of these, the bisacrylamides are preferable from a perspective of increased polymerization rate, and of these, N,N'-methylene bisacrylamide and N,N'-ethylene bisacrylamide are preferable. A range for the amount of monomer containing two or more polymeric groups that is used is between about 0.1 and about 10 weight %, in some embodiments between about 0.5 and about 8 weight %, and between about 0.8 and about 5 weight %, because a favorable lens shape can be obtained. Lower limit values include about 0.1 weight %, about 0.5 weight %, and about 0.8 weight %. Upper limit values include about 10 weight %, about 8 weight %, and about 5 weight %. Any of the preferred lower limit values and any of the preferred upper limit values can be combined together.

When obtaining the polymer of the present invention by polymerization a polymerization initiator may also be added to enhance polymerization. Suitable initiators include, thermal polymerization initiators such as a peroxide compound or an azo compound, or photopolymerization initiators. In some embodiments, photoinitiators are added in order to enhance polymerization. If thermal polymerization is used, a thermal polymerization initiator that has optimal decomposition properties at the desired reaction temperature is selected and used. Generally, an azo type initiator or a peroxide type initiator where the 10 hour half-life temperature is between about 40° C. and about 120° C. is preferable. Examples of photopolymerization initiators include carbonyl compounds, peroxide compounds, azo compounds, sulfur compounds, halogenated compounds, metal salts, and the like. More specific examples of photoinitiators include as aromatic alpha-hydroxy ketones, alkoxyoxybenzoins, acetophenones, acylphosphine oxides, bisacylphosphine oxides, and a tertiary amine plus a diketone, mixtures thereof and the like. Illustrative examples of photoinitiators are 1-hydroxycyclohexyl phenyl ketone, 2-hydroxy-2-methyl-1-phenyl-propan-1-one, bis(2,6-dimethoxybenzoyl)-2,4-4-trimethylpentyl phosphine oxide (DMBAPO), bis(2,4,6-trimethylbenzoyl)-phenyl phosphineoxide (Irgacure 819), 2,4,6-trimethylbenzyldiphenyl phosphine oxide and 2,4,6-trimethylbenzoyl diphenylphosphine oxide, benzoin methyl ether and a combination of camphorquinone and ethyl 4-(N,N-dimethylamino)benzoate. Commercially available visible light initiator systems include Irgacure 819, Irgacure 1700, Irgacure 1800, Irgacure 819, Irgacure 1850 (all from BASF) and Lucirin TPO initiator (available from BASF). Commercially available UV photoinitiators include Darocur 1173 and Darocur 2959 (BASF). These and other photoinitiators which may be used are disclosed in Volume III, Photoinitiators for Free Radical Cationic & Anionic Photopolymerization, 2$^{nd}$ Edition by J. V. Crivello & K. Dietliker; edited by G. Bradley; John Wiley and Sons; New York; 1998, which is incorporated herein by reference. These polymerization initiators can be used independently or blended together, and the amount used is approximately 1 weight % for 100 weight % of monomer component.

Other components that can be present in the reaction mixture used to form the contact lenses of this invention include, ultra-violet absorbing compounds, medicinal compounds, nutraceutical compounds, antimicrobial compounds, copolymerizable and nonpolymerizable dyes, including dyes and compounds which reversibly change color or reflect light when exposed to various wavelengths of light, release agents, reactive tints, pigments, combinations thereof and the like.

When obtaining the polymer of the present invention by polymerization, a polymerization solvent can be used. The solvent can be any type of organic or inorganic solvent. Solvents useful in preparing the devices of this invention include ethers, esters, alkanes, alkyl halides, silanes and alcohols. Examples of ethers useful as diluents for this invention include tetrahydrofuran. Examples of esters useful for this invention include ethyl acetate. Examples of alkyl halides useful as diluents for this invention include methylene chloride. Examples of silanes useful as diluents for this invention include octamethylcyclotetrasiloxane. Examples of alcohols useful as diluents for this invention include hexanol, heptanol, octanol, nonanol, decanol, tert-butyl alcohol, 3-methyl-3-pentanol, isopropanol, and 3,7-dimethyl-3-octanol. Additional diluents useful for this invention are disclosed in U.S. Pat. No. 6,020,445, which is incorporated herein by reference.

Examples that can be used include water, methanol, ethanol, propanol, 2-propanol, butanol, tert-butanol, tert-amyl alcohol, 3,7-dimethyl-3-octanol, tetrahydrolinalool, and other alcohol type solvents; benzene, toluene, xylene, and other types of aromatic hydrocarbon solvents; hexane, heptane, octane, decane, petroleum ether, kerosene, ligroin, paraffin, and other types of aliphatic hydrocarbon solvents; acetone, methyl ethyl ketone, methyl isobutyl ketone, and other ketone type solvents; ethyl acetate, butyl acetate, methyl benzoate, ethylene glycol diacetate, and other ester type solvents; diethyl ether, tetrahydrofuran, dioxane, ethylene glycol dialkyl ether, diethylene glycol dialkyl ether, triethylene glycol dialkyl ether, tetraethyleneglycol dialkyl ether, polyethylene glycol dialkyl ether, polyethylene glycol-poly propylene glycol block copolymer, polyethylene glycol-poly propylene glycol random copolymer, and other types of glycol ether solvents. The solvents can be used individually or combined. Of these, alcohol type solvents and glycol ether type solvents are preferable from a perspective that the solvents can easily be removed from the polymer obtained by washing with water.

The polymer of the present invention can be used independently by molding into the desired shape, but can also be blended with other materials and then molded. Furthermore, a coating is preferably applied to the surface of the molded parts.

Applications for the polymer of the present invention include ophthalmic lenses, endoscopes, catheters, transfusion tubes, gas transport tubes, stents, sheaths, cuffs, tube connectors, access ports, drainage bags, blood circuits, wound covering material, and various types of medicine carriers, but contact lenses, intraocular lenses, artificial cornea, cornea inlays, and cornea onlays are particularly suitable, and contact lenses are most suitable.

When the polymer of the present invention is molded and used as an ophthalmic lens, the polymerization method and molding method can be standard methods as follows. Examples include a method of first molding the silicone hydrogel into a round bar or plate and then machining to the desired shape by a cutting process or the like, a mold polymerization method, a spin cast method, and the like.

As one example, the case where an ophthalmic lens is made from the polymer of the present invention using a mold polymerization method is described next.

A monomer composition is injected into the space between two molds which have a lens shape. Next, photopolymerization or thermal polymerization is performed to form the lens shape. The mold is made from plastic, glass, ceramic, metal, or the like, but for the case of photo polymerization, an optically transparent material is used, and normally plastic or glass is used. When manufacturing the polymer, a space is formed by two counterfacing molds, and the monomer composition is injected into the space. Next, the mold with the space filled with the monomer composition is irradiated with an activating light such as ultraviolet light, visible light or a combination thereof, or placed in an oven or bath and heated to polymerize the monomer. It is also possible to use both methods, by thermal polymerization after photopolymerization or conversely by using photopolymerization after thermal polymerization. For the case of photopolymerization, generally a light containing a high level of light from a light source, such as a mercury lamp or a fluorescent lamp for example, is irradiated for a short period of time (normally 1 hour or less). When performing thermal polymerization, conditions where the temperature is gradually increased from near room temperature to a high temperature of between about 60° C. and about 200° C. over the course of several hours to several tens of hours is preferable in order to maintain the optical consistency and quality of the polymer and to increase the reproducibility.

The polymer of the present invention can optionally be modified by various methods. If the application is an ophthalmic lens, and a hydrophilic polymer is not internally included, a modification process may be performed in order to improve the wetting properties of the lens.

Specific modification methods include electromagnetic (including light) irradiation, plasma irradiation, vapor deposition, chemical vapor deposition treatment such as sputtering, heating, mold transfer coating, charge association coatings, base treatments, acid treatments, and treatments with other suitable surface treatment agents, and combinations thereof can also be used. Of these modification means, base treatments and acid treatments are preferable because they are simple.

Examples of a base treatment or acid treatment include a method of bringing a molded part into contact with a basic or acidic solution, or a method of bringing a molded part into contact with a basic or acidic gas. More specific methods include, for example, a method of immersing a molded parts in a basic or acidic solution, a method of spraying a basic or acidic solution or a basic or acidic gas onto a molded parts, a method of applying a basic or acidic solution onto a molded part using a paddle or brush or the like, a method of spin coating a basic or acidic solution onto a molded part, a dip coat method, and the like. The simplest method that provides a large modification affect is a method of immersing a molded part in a basic or acidic solution.

A temperature range when immersing the polymer in a basic or acidic solution is not particularly restricted, but normally the temperature is within a range between approximately about −50° C. and about 300° C. When considering an ease of work, a temperature range between about −10° C. and about 150° C. is more preferable, and a range between about −5° C. and about 60° C. is most preferable. A lower limit value is preferably about −50° C., more preferably about −10° C., and even more preferably about 5° C. An upper limit value is preferably about 300° C., more preferably about 150° C., and even more preferably about 60° C. Any of the preferred lower limit values and any of the preferred upper limit values can be combined together.

The optimum time that the polymer is immersed in the basic or acidic solution varies depending on the temperature, but generally 100 hours or less is preferable, 24 hours or less is more preferable, and 12 hours or less is most preferable. If the contact time is too long, not only will the ease of work and the productivity be inferior, but there may also be negative effects such as reducing the oxygen permeability and degrading the mechanical properties.

Examples of bases that can be used include alkali metal hydroxides, alkali earth metal hydroxides, various types of carbonates, various types of borates, various types of phosphates, ammonia, various ammonium salts, various amines, and polymer bases such as polyethyleneimine and polyvinyl amine and the like. Of these, alkali metal hydroxides are most preferable because of the low cost and the strong treatment effect.

Examples of acids that can be used include various types of inorganic acids such as sulfuric acid, phosphoric acid, hydrochloric acid, and nitric acid; various types of organic acids such as acetic acid, formic acid, benzoic acid, and phenol; and various types of polymer acids such as polyacrylic acid and polystyrene sulfonic acid and the like. Of these, polymer acids are most preferable because the treatment effect is strong and the negative effect on other physical properties is minimal.

The solvent for the basic or acidic solution can be any type of inorganic or organic solvent. Examples include water, methanol, ethanol, propanol, 2-propanol, butanol, ethylene glycol, diethylene glycol, triethylene glycol, tetraethyleneglycol, polyethylene glycol, glycerin, and other alcohols, benzene, toluene, xylene, and other aromatic hydrocarbons, hexane, heptane, octane, decane, petroleum ether, kerosene, ligroin, paraffin, and other aliphatic hydrocarbons, acetone, methyl ethyl ketone, methyl isobutyl ketone, and other ketones, ethyl acetate, butyl acetate, methyl benzoate, dioctyl phthalate, and other esters, diethyl ether, tetrahydrofuran, dioxane, ethylene glycol dialkyl ether, diethyl glycol dialkyl ether, triethylene glycol dialkyl ether, tetraethyleneglycol dialkyl ether, polyethylene glycol dialkyl ether and other ethers; dimethylformamide, dimethyl acetoamide, N-methyl-2-pyrrolidone, dimethyl imidazolidinone, hexamethyl phospholic triamide, dimethyl sulfoxide and other non-protonic polar solvents, methylene chloride, chloroform, dichloroethane, trichloroethane, trichloroethylene, other halogen type solvents, freon type solvents, and the like. Of these, water is most preferable from the perspective of economics, simplicity of handling, and chemical stability and the like. The solvent can also be a blend of two or more types.

With the present invention, the basic or acidic solution that is used may contain components other than the basic or acidic substance and the solvent.

The basic or acidic substance can be removed from the polymer by washing after the basic or acidic treatment.

The washing solvent can be any type of inorganic or organic solvent. Examples include water, methanol, ethanol, propanol, 2-propanol, butanol, ethylene glycol, diethylene glycol, triethylene glycol, tetraethyleneglycol, polyethylene glycol, glycerin, and other alcohols, benzene, toluene, xylene, and other aromatic hydrocarbons, hexane, heptane, octane, decane, petroleum ether, kerosene, ligroin, paraffin, and other aliphatic hydrocarbons, acetone, methyl ethyl ketone, methyl isobutyl ketone, and other ketones, ethyl acetate, butyl acetate, methyl benzoate, dioctyl phthalate, and other esters, diethyl ether, tetrahydrofuran, dioxane, ethylene glycol dialkyl ether, diethylene glycol dialkyl ether, triethylene glycol dialkyl ether, tetraethylene glycol dialkyl ether, polyethylene glycol dialkyl ether and other ethers; dimethylformamide, dimethyl acetoamide, N-methyl-2-pyrrolidone, dimethyl imidazolidinone, hexamethyl phospholic triamide, dimethyl sulfoxide and other non-protonic polar solvents, methylene chloride, chloroform, dichloroethane, trichloroethane, trichloroethylene, other halogen type solvents, and freon type solvents.

The washing solvent can be a blend of two or more types. The washing solvent can contain components other than solvent, such as inorganic salts, surfactants, and cleaning agents.

Modification treatment as described above can be performed on the entire polymer or can be performed only on a portion of the polymer such as only on the surface. If the modifications are performed only on the surface, the surface wet ability alone can be enhanced without dramatically changing the physical properties of the entire polymer.

If a water content range of the polymer of the present invention is too low, the silicone hydrogel will be hard, but if the water content is too high, water may evaporate from the surface of the silicone hydrogel and the wearer may a dry lens feeling during lens wear, so water content between about 20 and about 50 weight % are desirable, between about 25 and about 45 weight % is more preferable, and between about 30 and about 40 weight % is most preferable. Lower limit values include about 20 weight %, about 25 weight %, and about 30 weight %. Upper limit values are about 50 weight %, about 45 weight %, and about 40 weight %. Any of the preferred lower limit values and any of the preferred upper limit values can be combined together.

An elastic modulus of the polymer of the present invention is about 200 psi or less, in some embodiments less than about 150 psi or less, and in other embodiments less than about 100 psi or less, in order to obtain comfortable feel when being worn when the use is an ophthalmic lens and particularly a soft contact lens.

An elongation of the polymer of the present invention is about 100% or higher, in some embodiments about 150% or higher, and in other embodiments about 200% or higher. Higher elongation values mean that the silicone hydrogel will not easily break. The elastic modulus and elongation of the polymer of the present invention are measured by cutting out an array shape sample where a width of the narrowest section is 5 mm, and then stretching at a rate of 100 mm/minute using a tensile tester.

An advancing contact angle of the polymer of the present invention is about 70 degrees or less, about 60 degrees or less, and in some embodiments about 50 degrees or less, if the application is an ophthalmic lens. The advancing contact angle of the polymer of the present invention is obtained by measuring a short strip sample with a width of 5 mm cut from a lens shaped sample, at an immersion rate of 7 mm/minutes using a dynamic contact angle meter.

As for the oxygen permeability of the polymer of the present invention, the oxygen permeability constant is desirably $50 \times 10^{-11}$ (cm$^2$/sec) mL O$_2$/ (mL·hPa) or higher and in some embodiments $50 \times 10^{-11}$(cm$^2$/sec)mLO$_2$/(mL·hPa) or higher. The oxygen permeability constant of the polymer of the present invention is a value measured by a polarographic method.

As for the transparency of the polymer of the present invention, the whole light transmissivity is desirably about 85% or higher, about 88% or higher, and about 91% or higher when the application is an ophthalmic lens. The whole light transmissivity of the polymer of the present invention is obtained by lightly wiping the water from a lens shaped sample with a thickness between 0.14 and 0.15 mm, setting the sample in the light path of a light transmissivity measuring apparatus, and then measuring the whole light transmissivity.

A value that expresses the shape recovery properties of the polymer of the present invention is a stress zero time measured by a measurement method described later. A shorter stress zero time indicates that the shape recovery properties of the silicone hydrogel are favorable, and a value of 1 second or less is desirable, 0.95 seconds or less is more preferable, and 0.9 seconds or less is most preferable. Measurement of the stress zero time of the polymer of the present invention is performed by the following method. A 5 mm wide 1.5 cm long strip sample was cut from near the center of a lens, and measured using a dynamic viscoelasticity measuring device. The sample was mounted at a chuck width of 5 mm, and after stretching 5 mm at a rate of 100 mm/minute, this sample was returned to the original length (5 mm) at the same rate, and this cycle was repeated 3 times. From the moment that the stress became zero part way through returning the sample to the original length the second time, the length of time until the moment that stress began to be applied (stress was no longer zero) after beginning the third stretch cycle was determined to be the stress zero time.

The polymer obtained by polymerizing the silicone monomer of the present invention is suitable for various medical implements such as ophthalmic lenses, endoscopes, catheters, transfusion tubes, gas transport tubes, stents, sheaths, cuffs, tube connectors, access ports, drainage [bags], blood circuits, wound covering material, and various types of medicine carriers, but is particularly suitable for contact lenses, intraocular lenses, and artificial corneas.

The present invention will be described in further detail below through the use of working examples, but the present invention is not limited to these working examples.

Measurement Method (1) GC Measurement

Device

Shimadzu GC-18A (FID detector)

Capillary column

Agilent HP-ULTRA2 (length 25 m×inner diameter 0.32 mm×film thickness 0.52 micrometers)

Temperature program

Injection port temperature: 300° C.

Detector temperature: 320° C.

Column temperature: Initial temperature 50° C. (1 minute) →increased temperature at rate of 10° C./minute→300° C. (maintain for 14 minutes) (total 40 minutes)

Carrier gas

Helium gas (110 kPa)

Sample Preparation

100 μL of reaction solution diluted with 1 mL of solvent (toluene, 2-propanol, or ethyl acetate) was used as the sample.

(2) Whole Light Transmissivity

The whole light transmissivity was measured using an SM color computer (model SM-7-CH, manufactured by Suga Test Instruments Co. Ltd.). Water on the lens sample is lightly wiped off, and then the sample is set in the light path and measured. The thickness was measured using an ABC Digimatic Indicator (ID-C112, manufactured by Mitsutoyo Corporation), and samples with a thickness between 0.14 and 0.15 mm were measured.

(3) Elastic Modulus and Elongation

An array shaped sample with a width of 5 mm in the narrowest region was cut from the lens sample, the thickness was measured using an ABC Digimatic Indicator (ID-C112, manufactured by Mitsutoyo 100 mm/minute, and then the elastic modulus and the elongation were measured using a Tensilon (RTM-100 manufactured by Toyo Baldwin Co. Ltd., cross head speed 100 mm/minute).

(4) Water Content

The weight of the silicone hydrogel when containing water (W1) and the weight when dry (W2) were measured and the water content was calculated from the following formula.

$$\text{Water content}(\%) = (W1 - W2)/W1 \times 100$$

However, with the present invention, the condition where the silicone hydrogel contains water refers to a condition where the silicone hydrogel has been immersed in saline solution water at 25° C. for 6 hours or longer. Furthermore, a dry condition for the silicone hydrogel refers to a condition where drying has been performed for 16 hours or longer in a vacuum dryer at 40° C.

(5) Advancing Contact Angle

A short strip sample with a width of 5 mm was cut from the lens sample, and the dynamic contact angle was measured (advancing and receding) using a WET-6000 dynamic contact angle meter manufactured by Rhesca Corporation (immersion rate 7 mm/minute). After obtaining the measurement value, the value for the advancing contact angle was used as an indicator of the wettability.

(6) Stress Zero Time

A 5 mm wide 1.5 cm long strip sample was cut from near the center of a lens, and measured using a CR-500DX rheometer manufactured by Sun Scientific Co. Ltd. The sample was mounted at a chuck width of 5 mm, and after stretching 5 mm at a rate of 100 mm/minute, this sample was returned to the original length (5 mm) at the same rate, and this cycle was repeated 3 times. From the moment that the stress became zero part way through returning the sample to the original length the second time, the length of time until the moment that stress began to be applied (stress was no longer zero) after beginning the third stretch cycle was determined to be the stress zero time.

(7) Conversion by DSC

Thermal analysis of the cure of a reactive monomer mix (RMM) was carried out using photo-differential scanning calorimetry (photo-DSC). A sample of ~10 mg of the RMM under consideration was weighed into a DSC pan and placed, along with an empty reference pan, onto the stage of a Q100 DSC from TA Instruments. The sample chamber was purged with dry nitrogen (50 mL/min) during the analysis. The sample was heated to 70° C., an LED light source (~420 nm, 4.0 mW/cm$^2$) was triggered to activate the photoinitiator and the heat evolved (enthalpy, J/g) during isothermal cure for 10 minutes was measured. The total enthalpy was derived from integration of the area of the DSC trace of enthalpy over time and the percent conversion at various time points was calculated.

SYNTHESIS EXAMPLE 1

28 to 30 weight percent ammonia water (320 mL) and methanol (48 mL) were placed in a 500 mL 4-necked flask, and a mechanical stirrer, dropping funnel, reflux condenser, and glass stopper were attached. A solution of allyl glycidyl ether (59.6 g, 0.522 mol)/methanol (48 mL) was added dropwise into the flask over the course of approximately 9 hours while maintaining the 4-necked flask at a temperature of approximately 25° C. using a circulator. Completion of the reaction was confirmed using GC.

After the reaction was complete, the reaction solution was concentrated in an evaporator. The liquid obtained was purified using distillation under reduced pressure (full vac., 81° C.). The yield was 31.6 g (46.1% yield) and the GC purity was 99.0%.

SYNTHESIS EXAMPLE 2

The compound obtained in synthesis example 1 (30.0 g, 0.229 mol), hexamethyldisilazane (22.2 g, 0.137 mol), BHT (0.09 g), and saccharine (0.09 g) were placed in a 200 mL 4-necked flask and mixed for 2 hours at 100° C.

The reaction was ended after confirming the elimination of the raw material peaks using GC measurement. After purifying by distillation under reduced pressure (full vac., 72° C.), the yield was 39.0 g (yield rate 83.9%), and the GC purity was 99.4%.

SYNTHESIS EXAMPLE 3

The compound obtained by synthesis example 2 (38.0 g, 0.187 mol), 1-n-butyl-1,1,3,3,5,5,7,7,9,9-decamethylpentasiloxane expressed by the following formula

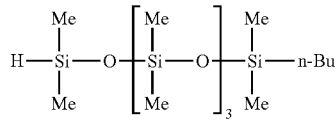

(hereinafter referred to as "SiL5B") (77.2 g, 0.187 mol), a 0.104 M methylvinyl cyclosiloxane solution of platinum (0) 2,4,6,8-tetramethyl-2.4.6.8-tetravinyl cyclotetrasiloxane complex (manufactured by Aldrich Corp., hereinafter referred to as "platinum tetra solution") (610 μL, and toluene (370 μL) were placed in a 200 mL 4-necked flask, and then heated to 120° C. and mixed.

After 2 hours, an additional 610 μL of platinum tetra solution was added because raw material was found to be remaining by the GC measurement, and the reaction was continued for another hour. After confirming elimination of the raw materials by GC, the solution was cool to room temperature and concentrated in an evaporator. The liquid obtained was purified by distillation under reduced pressure ($8\times10^{-2}$ Pa, 156° C.) using an oil diffusion pump. The yield was 65.5 g (56.9% yield), and the GC purity was 95.0%.

SYNTHESIS EXAMPLE 4

The compound obtained by synthesis example 3 (64.0 g, 0.104 mol), triethylamine (10.5 g, 0.104 mol) and hexane (170 mL) were placed in a 500 mL 4-necked flask, acryloyl chloride (9.40 g, 0.104 mol) and hexane (130 mL) were added by drops using a dropping funnel over a period of approximately 6 hours while in an ice bath (−1 to 2° C.). 40 minutes after dropwise addition was complete, A GC measurement was performed and it was confirmed that nearly all of the raw materials were exhausted.

One hour after the start of dropwise addition, the reaction solution was filtered and the precipitate was washed with hexane that had been cooled in a refrigerator. The wash solution was combined with the filtrate, transferred to a separation funnel, and washed three times with water (300 mL), two times with a saturated aqueous solution of sodium hydrogen carbonate (300 mL) and two times with a saturated aqueous solution of sodium chloride (300 mL).

The organic layer was dried overnight using sodium sulfate, filtered, and then concentrated using an evaporator. The yield of the crude material obtained was 58.7 g (84.3% crude yield).

WORKING EXAMPLE 1

The crude product obtained by Synthesis Example 4 (57.0 g, 0.085 mol), methanol (171 g), and acetic acid (28.5 g) were placed in a 300 mL eggplant flask and mixed for approximately 1 hour at 40° C.

Exhaustion of raw materials was confirmed using TLC, and after concentrating in an evaporator, 350 mL of hexane was added, and the solution was transferred to a separation funnel The solution was washed two times each with water (250 mL), a saturated aqueous solution of sodium hydrogen carbonate (250 mL), and a saturated aqueous solution of sodium chloride (250 mL). The organic layer was dried overnight using sodium sulfate, filtered, and then concentrated using an evaporator. The yield of the crude material was 50.83 g.

23.63 g of the crude material was purified in a column. The weight of silica gel used was approximately 5 times (120 g) the weight of the crude material. Elution was performed by TLC using hexane/ethyl acetate=1/1 until the target spot was eliminated. Several fractions were measured by a GC at both ends of the recovery range and the range of the fractions where all by product peaks were less than 1% were measured and collected. 6.0 mg of BHT and 2.0 mg of MEHQ were added and concentrated, and then the pressure was reduced using a vacuum pump while mixing for an additional 1 hour at 60° C. to remove the residual solvent. It was confirmed that a solvent peak was not observed using NMR. The yield was 20.14 g (85.2% yield), and the GC purity was 95.2%.

SYNTHESIS EXAMPLE 5

Allylamine (112.4 mL, 85.54 g, 1.5 mol) was placed in a 4-necked flask and a reflex condenser, thermometer, dropping funnel, and mechanical stirrer were attached. Glycidol (2,3-epoxy-1-propanol, 37.8 g, 0.5 mol) was added to the dropping funnel, and added by drops over approximately 10 minutes while mixing at 30° C. A GC measurement was performed each hour starting at the time that dropwise addition was completed in order to confirm the progress of the reaction. 5 hours after dropwise addition was completed it was confirmed that the glycidol peak was 1% or less and the reaction was terminated. The solution was concentrated in an evaporator, and then purified by reduced pressure installation (full vac, bp 52° C.). The yield was 27.43 g (41.8% yield), and the GC purity was 98.7%.

SYNTHESIS EXAMPLE 6

The compound obtained in synthesis example 5 (23.2 g, 0.177 mol), hexamethyldisilazane (33.89 g, 0.210 mol), BHT (72 mg), and saccharine (70 mg) were placed in a 4-necked flask and a reflex condenser, thermometer, and mechanical stirrer were attached. The reaction was performed for 2 hours at 100° C. and the reaction was terminated after confirming that the reactants were reduced or exhausted using GC. The reaction solution was concentrated in an evaporator, and then purified by distillation under reduced pressure (full vac, bp 77° C.). The yield was 36.31 g (70.2% yield), and the GC purity was 98.4%.

SYNTHESIS EXAMPLE 7

The compound obtained by synthesis example 6 (35.0 g, 0.127 mol), SiL5B (52.4 g, 0.127 mol), toluene (263 mL), and platinum tetra solution (350 µL) were placed in a 1 L 3-necked flask and a reflux condenser, thermometer, and mechanical stirrer were attached. The reaction was performed at 120° C. while making GC measurements each hour. An additional 350 µL of platinum tetra solution was added because raw material was remaining after 4 hours. The solution was heated and stirred for an additional 4 hours and then the reaction was terminated. The reaction solution was concentrated in an evaporator, and then purified by distillation under reduced pressure ($8 \times 10^{-2}$ Pa, 176° C.). The yield was 58.22 g (66.6% yield) and the GC purity was 96.2%.

SYNTHESIS EXAMPLE 8

The compound obtained by synthesis example 7 (55 g, 0.080 mol), triethylamine (8.08 g, 0.080 mol), and ethyl acetate (130 mL) were placed in a 1 L 3-necked flask and a dropping funnel, thermometer, and mechanical stirrer were attached. Acryloyl chloride (7.23 g, 0.080 mol) and ethyl acetate (100 mL) were placed in the dropping funnel The 3-necked flask was placed in an ice bath containing salt and dropwise addition was started after waiting for the internal temperature to drop to 0° C. While maintaining the internal temperature between −2 and 3° C., dropwise addition was performed over approximately 3 hours and after dropwise addition was completed, the reaction was continued for another hour and then terminated. The solution was then filtered while washing with a small amount of chilled ethyl acetate that had been chilled in a refrigerator. The filtrate was transferred to a separation funnel and 400 mL off hexane was added. The solution was washed two times with water (200 mL), two times with a saturated aqueous solution of sodium hydrogen carbonate (200 mL), and two times with a saturated aqueous solution of sodium chloride (200 mL). Anhydrous sodium sulfate was added to the organic layer and drying was performed overnight. After filtering, this solution was concentrated in an evaporator to obtain crude product. The crude yield was 54.6 g and the GC purity was 88.5%.

WORKING EXAMPLE 2

The crude product obtained by synthesis example 8 (54.6 g, 0.074 mol), 3 parts (weight ratio) of methanol (163.8 g) and one half part (weight ratio) of acetic acid (27.3 g) was added for each part of crude product, and then the solution was mixed for 1 hour at 40° C. After reacting, the solution was concentrated in an evaporator.

The liquid obtained (70.5 g) was transferred to a separation funnel, and 4 parts of hexane (volumetric ratio) (280 g) were added to one part of liquid. The solution was washed two times each with water (210 mL), a saturated aqueous solution of sodium hydrogen carbonate (200 mL), and a saturated aqueous solution of sodium chloride (250 mL), and then the organic layer was dried overnight using anhydrous sodium sulfate. The solution was concentrated in an evaporator to obtain 35.03 g of crude material. 35 g of the crude material was purified in a column. The amount of silica gel used was five times the weight of the crude material (175 g). For the solvent, hexane/ethyl acetate=5/1 was used until impurities were discharged (2.48 L), and after confirming that the impurities had been discharged, the target material was eluted using hexane/ethyl acetate=1/3 (1.6 L). The range of the fraction containing the target material was confirmed using TLC, and several fractions on both ends of this range were measured by GC, and only fractions where the byproducts were less than 1% were collected. 6.0 mg of BHT and 2.0 mg of MEHQ were added and the solution was concentrated in an evaporator. The solution was stirred at 60° C. while reducing the pressure using a vacuum pump for 1 hour in order to remove the remaining solvent, and it was confirmed that a residual solvent peak was not observed using NMR. The yield was 18.69 g (43% yield) and the GC purity was 95.2%.

SYNTHESIS EXAMPLE 9

40 weight % methylamine in water (233 g, 3.0 mol) and methanol (35 mL) were placed in a 500 mL 4-necked flask, and a mechanical stirrer, dropping funnel, reflux condenser, and glass stopper were attached. A solution of allyl glycidyl ether (34.2 g, 0.3 mol)/methanol (35 mL) was added dropwise into the flask over the course of approximately 5 hours while maintaining the 4-necked flask at a temperature of approximately 25° C. using a circulator. Completion of the reaction was confirmed using GC.

After the reaction was complete, the reaction solution was concentrated in an evaporator. The liquid obtained was purified using distillation under reduced pressure (full vac., 76° C.). The yield was 35.3 g (81% yield) and the GC purity was 99.2%.

SYNTHESIS EXAMPLE 10

The compound obtained in Synthesis Example 9 (16.6 g, 0.114 mol), hexamethyldisilazane (11.2 g, 0.069 mol), BHT (0.05 g), and saccharine (0.05 g) were placed in a 100 mL 3-necked flask and mixed for 3 hours at 100° C.

The reaction was ended after confirming the elimination of the raw material peaks using GC measurement. After purifying by distillation under reduced pressure (full vac., 68° C.), the yield was 22.31 g (90% yield), and the GC purity was 99%.

SYNTHESIS EXAMPLE 11

The compound obtained by Synthesis Example 10 (5.0 g, 0.023 mol), SiL5B (9.50 g, 0.023 mol), toluene (46 mL), and platinum tetra solution (80 µL) were placed in a 300 mL 3-necked flask and a reflux condenser, thermometer, and mechanical stirrer were attached. The reaction was performed at 50° C. for 1.5 hours. The reaction solution was concentrated in an evaporator, and then purified by distillation under reduced pressure (0.02 mmHg, 135° C.). The yield was 8.3 g (57% yield) and the GC purity was 93%.

SYNTHESIS EXAMPLE 12

The compound obtained by Synthesis Example 11 (20.0 g, 0.032 mol), triethylamine (3.21 g, 0.032 mol) and hexane (54 mL) were placed in a 200 mL 3-necked flask, acryloyl chloride (3.1 mL, 0.038 mol) and hexane (32 mL) were added by drops using a dropping funnel over a period of approximately 2 hours while in an ice bath (−10 to −5° C.). 40 minutes after dropwise addition was complete, A GC measurement was performed and it was confirmed that nearly all of the raw materials were exhausted.

One hour after the start of dropwise addition, the reaction solution was filtered and the precipitate was washed with hexane that had been cooled in a refrigerator. The wash solution was combined with the filtrate, transferred to a separation funnel, and washed three times with water (50 mL), two times with a saturated aqueous solution of sodium hydrogen carbonate (50 mL) and two times with a saturated aqueous solution of sodium chloride (50 mL).

The organic layer was dried overnight using sodium sulfate, filtered, and then concentrated using an evaporator. The yield of the crude material obtained was 21.6 g (94% crude yield).

WORKING EXAMPLE 3

The crude product obtained by Synthesis Example 12 (12.0 g, 0.017 mol), methanol (36 g), and acetic acid (5 mL) were placed in a 100 mL eggplant flask and mixed for approximately 1 hour at 40° C.

Exhaustion of raw materials was confirmed using TLC, and after concentrating in an evaporator, 50 mL of hexane was added, and the solution was transferred to a separation funnel The solution was washed two times each with water (40 mL), a saturated aqueous solution of sodium hydrogen carbonate (40 mL), and a saturated aqueous solution of sodium chloride (40 mL). The organic layer was dried overnight using sodium sulfate, filtered, and then concentrated using an evaporator. The yield of the crude material was 11.1 g.

10.00 g of the crude material was purified in a column. The weight of silica gel used was approximately 5 times (50 g) the weight of the crude material. Elution was performed by TLC using hexane/ethyl acetate=1/3 until the target spot was eliminated. Several fractions were measured by a GC at both ends of the recovery range and the range of the fractions where all by product peaks were less than 1% were measured and collected. 3.0 mg of BHT and 1.0 mg of MEHQ were added and concentrated, and then the pressure was reduced using a vacuum pump while mixing for an additional 1 hour at 60° C. to remove the residual solvent. It was confirmed that a solvent peak was not observed using NMR. The yield was 11.4 g (78% yield), and the GC purity was 98%.

SYNTHESIS EXAMPLE 13

Diallylamine (2.49 mL, 0.02 mol), SiL5B (24.76 g, 0.06 mol), toluene (40 mL), and platinum tetra solution (0.07 mL) were placed in a 200 mL 3-necked flask and a reflux condenser, thermometer, and mechanical stirrer were attached. The reaction was performed at 100° C. for 3 hours. The reaction solution was concentrated in an evaporator, and then low-boiling-point impurities was distilled off under reduced pressure (0.02 mmHg, 97° C.). The yield was 14.46 g (74% yield).

WORKING EXAMPLE 4

The compound obtained by Synthesis Example 13 (9.2 g, 0.01 mol), triethylamine (1.8 mL, 0.013 mol) and hexane (15 mL) were placed in a 100 mL 3-necked flask, acryloyl chloride (1.05 mL, 0.013 mol) was added by drops using a syringe. 40 minutes after dropwise addition was complete, A GC measurement was performed and it was confirmed that nearly all of the raw materials were exhausted.

2 hours after the start of dropwise addition, the reaction solution was filtered and the precipitate was washed with hexane that had been cooled in a refrigerator. The wash solution was combined with the filtrate, transferred to a separation funnel, and washed three times with water (50 mL), two times with a saturated aqueous solution of sodium hydrogen carbonate (50 mL) and two times with a saturated aqueous solution of sodium chloride (50 mL).

The organic layer was dried overnight using sodium sulfate, filtered, and then concentrated using an evaporator. The yield of the crude material obtained was 9.99 g. 3.1 g of the crude material was purified by preparative GPC and 2.06 g of purified silicone acrylamide monomer expressed by the following formula (s1) was obtained.

[FORMULA]

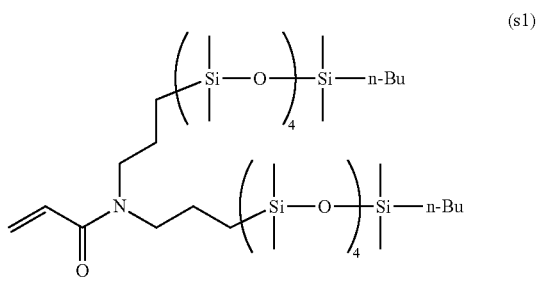

(s1)

SYNTHESIS EXAMPLE 14

Allylamine (5.0 g, 87 mmol), SiL5B (39.50 g, 95.7 mmol), toluene (100 mL), and platinum tetra solution (100 μL) were placed in a 300 mL 4-necked flask and a reflux condenser, thermometer, and mechanical stirrer were attached. The reaction was performed at 110° C. for 3 hours. The reaction solution was concentrated in an evaporator, and then purified by distillation under reduced pressure (0.17 mmHg, 118° C.). The yield was 32.93 g (81% yield) and the GC purity was 96%.

WORKING EXAMPLE 5

The compound obtained by Synthesis Example 14 (4.67 g, 0.01 mol), triethylamine (1.8 mL, 0.013 mol) and hexane (15 mL) were placed in a 100 mL 3-necked flask, acryloyl chloride (1.05 mL, 0.013 mol) and hexane (32 mL) were added by drops using a syringe while in an ice bath (−10 to −5° C.). 40 minutes after dropwise addition was complete, A GC measurement was performed and it was confirmed that nearly all of the raw materials were exhausted.

2 hours after the start of dropwise addition, the reaction solution was filtered and the precipitate was washed with hexane that had been cooled in a refrigerator. The wash solution was combined with the filtrate, transferred to a separation funnel, and washed three times with water (50 mL), two times with a saturated aqueous solution of sodium hydrogen carbonate (50 mL) and two times with a saturated aqueous solution of sodium chloride (50 mL).

The organic layer was dried overnight using sodium sulfate, filtered, and then concentrated using an evaporator. The yield of the crude material obtained was 5.31 g. The crude material was purified by column chromatography (hexane/ethyl acetate=4/1 to 2/1 as eluent, yield: 31.3%).

SYNTHESIS EXAMPLE 15

N-methyl-N-allylamine (5.11 g, 71.8 mmol), SiL5B (24.7 g, 60 mmol), toluene (120 mL), and platinum tetra solution (100 μL) were placed in a 300 mL 4-necked flask and a reflux condenser, thermometer, and mechanical stirrer were attached. The reaction was performed at 110° C. for 2 hours. The reaction solution was concentrated in an evaporator, and then purified by distillation under reduced pressure (0.17 mmHg, 115° C.). The yield was 20.34 g (70% yield) and the GC purity was 96%.

WORKING EXAMPLE 6

The compound obtained by Synthesis Example 15 (4.84 g, 0.01 mol), triethylamine (1.8 mL, 0.013 mol) and hexane (15 mL) were placed in a 100 mL 3-necked flask, acryloyl chloride (1.05 mL, 0.013 mol) was added by drops using a syringe while in an ice bath (−10 to −5° C.). 40 minutes after dropwise addition was complete, A GC measurement was performed and it was confirmed that nearly all of the raw materials were exhausted.

2 hour after the start of dropwise addition, the reaction solution was filtered and the precipitate was washed with hexane that had been cooled in a refrigerator. The wash solution was combined with the filtrate, transferred to a separation funnel, and washed three times with water (50 mL), two times with a saturated aqueous solution of sodium hydrogen carbonate (50 mL) and two times with a saturated aqueous solution of sodium chloride (50 mL).

The organic layer was dried overnight using sodium sulfate, filtered, and then concentrated using an evaporator. The yield of the crude material obtained was 5.45 g. The crude material was purified by column chromatography (hexane/ethyl acetate=5/1 to 3/1 as eluent) and 1.06 g of purified silicone acrylamide monomer was obtained.

WORKING EXAMPLE 7

The silicone monomer expressed by the following formula (s2)

[FORMULA 6]

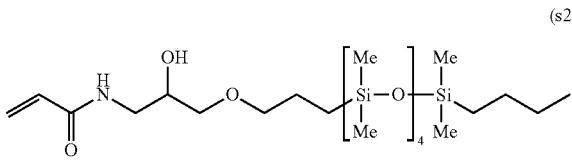

(s2)

that was obtained in working example 1 (0.925 g, 56.06 weight %), N,N-dimethyl acrylamide (0.510 g, 30.91 weight %), and the hydrophilic acrylamide monomer expressed by the following formula (h1)

[FORMULA 7]

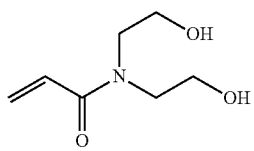

(h1)

(0.017 g, 1 weight %, polyvinyl pyrrolidone (PVP K90, 0.132 g, 8 weight %), N,N'-methylene bisacrylamide (MBA, 0.018 g, 1.10 weight %), UV absorber 2-(2'-hydroxy-5'-methacryloyloxyethylphenyl)-2H-benzotriazole (0.036 g, 2.20 weight %), 3-methyl-3-pentanol (3M3P, 1.350 g), and photoinitiator Irgacure 819 (0.004 g, 0.25 weight %) were blended and mixed together. The monomer mix obtained was degassed in an argon environment. The monomer mix was injected into the cavity in a transparent plastic (front curve side: Zeonor, base curve side: polypropylene) mold with a lens shape in a glove box under a nitrogen gas environment, and a lens was obtained by irradiating with light (Philips TL03, 1.6 mW/cm2, 15 minutes) to harden. The lens obtained was peeled from the mold and impurities such as residual monomer were extracted by immersing for 70 minutes at room temperature in a 70% (volumetric ratio) aqueous solution of 2-propanol (IPA). After immersing in water for 10 minutes, the sample was placed submerged in a boric acid buffer solution (pH 7.1 to 7.3) in a 5 mL vial bottle, and the vial bottle was placed in an autoclave and boiled for 30 minutes at 120° C.

The whole light transmissivity, water content, elastic modulus, and elongation of the lens sample obtained were as shown in Table 1, and thus a lens was obtained which was transparent and had a balance between favorable physical properties.

WORKING EXAMPLE 8

A lens shaped sample was fabricated in a manner similar to Working Example 7, except that the silicone acrylamide monomer of the following formula (s3)

[FORMULA 8]

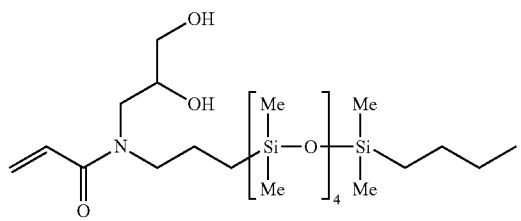

(s3)

obtained by working example 2 was used as the silicone acrylamide monomer in place of the monomer expressed by formula (s2). The whole light transmissivity, water content, elastic modulus, and elongation of the lens sample obtained were as shown in Table 1, and thus a lens was obtained which was transparent and had a balance between favorable physical properties.

WORKING EXAMPLE 9

A lens shaped sample was fabricated in a manner similar to Working Example 7, except that the silicone acrylamide monomer of the following formula (s4)

[FORMULA 9]

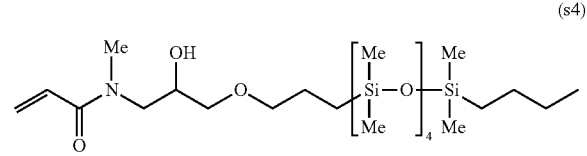

(s4)

obtained by Working Example 3 was used as the silicone acrylamide monomer in place of the monomer expressed by formula (s2), and except that the content of monomer mix was as follows; silicone acrylamide monomer (s4) (0.925 g, 56.06 weight %), N,N-dimethyl acrylamide (0.552 g, 33.27 weight %), the hydrophilic acrylamide monomer (h1) (0.116 g, 7 weight %), N,N'-methylene bisacrylamide (MBA, 0.0 18 g, 1.10 weight %), UV absorber 2-(2'-hydroxy-5'-methacryloyloxyethylphenyl)-2H-benzotriazole (0.0 36 g, 2.20 weight %), 3-methyl-3-pentanol (3M3P, 1.350 g), and photoinitiator Irgacure 819 (0.004 g, 0.25 weight %). The whole light transmissivity, water content, elastic modulus, and elongation of the lens sample obtained were as shown in Table 1, and thus a lens was obtained which was relatively transparent and had a balance between favorable mechanical properties. Wettability as measured by contact angle was higher than generally desired.

WORKING EXAMPLE 10

A lens shaped sample was fabricated in a manner similar to Working Example 7, except that the content of monomer mix was as follows; silicone acrylamide monomer (s2) (1.21 g, 55 weight %), N,N-dimethyl acrylamide (0.78 g, 35.53 weight %), polyvinyl pyrrolidone (PVP K90, 0.088 g, 4 weight %), tetraethylene glycol dimethacrylate (TEGMA, 0.066 g, 3 weight %), UV absorber 2-(2'-hydroxy-5'-methacryloyloxyethylphenyl)-2H-benzotriazole (0.048 g, 2.20 weight %), 3-methyl-3-pentanol (3M3P, 1.80 g), and photoinitiator Irgacure 819 (0.006 g, 0.25 weight %). The whole light transmissivity, water content, elastic modulus, and elongation of the lens sample obtained were as shown in Table 1, and thus a lens was obtained. Water content and mechanical properties were favorable, but whole lens transmissivity was low indicating an undesirably hazy lens and contact angle was higher than generally desired.

WORKING EXAMPLE 11

A lens shaped sample was fabricated in a manner similar to Working Example 10, except that the silicone acrylamide monomer expressed by the formula (s3) was used as the silicone acrylamide monomer in place of the monomer expressed by formula (s2). The whole light transmissivity, water content, elastic modulus, and elongation of the lens sample obtained were as shown in Table 1, and thus a lens was obtained. Water content and mechanical properties were favorable (including a desirable low modulus), and whole lens transmissivity was improved compared to Working Example 10. Contact angle was higher than generally desired.

WORKING EXAMPLE 12

A lens shaped sample was fabricated in a manner similar to Working Example 7, except that the content of monomer mix was as follows; silicone acrylamide monomer (s2) (1.21 g, 55 weight %), N,N-dimethyl acrylamide (0.43 g, 19.53 weight %), 2-hydroxyethyl methacrylate (0.176 g, 8 weight %), polyvinyl pyrrolidone (PVP K90, 0.264 g, 12 weight %), tetraethylene glycol dimethacrylate (TEGMA, 0.066 g, 3 weight %), UV absorber 2-(2'-hydroxy-5'-methacryloyloxyethylphenyl)-2H-benzotriazole (0.048 g, 2.20 weight %), 3-methyl-3-pentanol (3M3P, 1.80 g), and photoinitiator Irgacure 819 (0.006 g, 0.25 weight %). The whole light transmissivity, water content, elastic modulus, and elongation of the lens sample obtained were as shown in Table 1, and thus a lens was obtained which was transparent and had a balance between favorable physical properties.

WORKING EXAMPLE 13

A lens shaped sample was fabricated in a manner similar to Working Example 12, except that the silicone acrylamide monomer expressed by the formula (s3) was used as the silicone acrylamide monomer in place of the monomer expressed by formula (s2). The whole light transmissivity, water content, elastic modulus, and elongation of the lens sample obtained were as shown in Table 1, and thus a lens was obtained which was transparent and had a balance between favorable physical properties.

WORKING EXAMPLE 14

A lens shaped sample was fabricated in a manner similar to Working Example 7, except that the silicone acrylamide monomer of the following formula (s5)

[FORMULA]

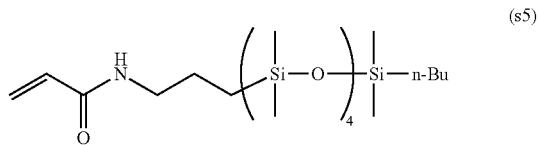

(s5)

obtained by Working Example 18 was used as the silicone acrylamide monomer in place of the monomer expressed by formula (s2), and except that the content of monomer mix was as follows; silicone acrylamide monomer (s5) (0.925 g, 56.06 weight %), N,N-dimethyl acrylamide (0.419 g, 25.27 weight %), polyvinyl pyrrolidone (PVP K90, 0.132 g, 8 weight %), the hydrophilic acrylamide monomer (h1) (0.116 g, 7 weight %), N,N'-methylene bisacrylamide (MBA, 0.0 18 g, 1.10 weight %), UV absorber 2-(2'-hydroxy-5'-methacryloyloxyethylphenyl)-2H-benzotriazole (0.0 36 g, 2.20 weight %), t-amyl alcohol (TAA, 1.350 g), and photoinitiator Irgacure 819 (0.004 g, 0.25 weight %). The whole light transmissivity, water content, elastic modulus, and elongation of the lens sample obtained were as shown in Table 1, and thus a lens was obtained which had a balance of favorable physical properties including a desirable modulus. Whole lens transmissivity was low indicating an undesirably hazy lens.

WORKING EXAMPLE 15

A lens shaped sample was fabricated in a manner similar to Working Example 7, except that silicone acrylamide monomer of the following formula (s6)

[FORMULA]

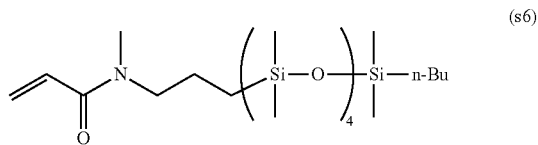

(s6)

obtained by Working Example 18 was used as the silicone acrylamide monomer in place of the monomer expressed by formula (s2), and except that the content of monomer mix was as follows; silicone acrylamide monomer (s6) (0.925 g, 56.06 weight %), N,N-dimethyl acrylamide (0.419 g, 25.27 weight %), polyvinyl pyrrolidone (PVP K90, 0.132 g, 8 weight %), the hydrophilic acrylamide monomer (h1) (0.116 g, 7 weight %), N,N'-methylene bisacrylamide (MBA, 0.0 18 g, 1.10 weight %), UV absorber 2-(2'-hydroxy-5'-methacryloyloxy-ethylphenyl)-2H-benzotriazole (0.0 36 g, 2.20 weight %), t-amyl alcohol (TAA, 1.350 g), and photoinitiator Irgacure 819 (0.004 g, 0.25 weight %). The whole light transmissivity, water content, elastic modulus, and elongation of the lens sample obtained were as shown in Table 1, and thus a lens was obtained which had a balance of favorable physical properties, including a desirable modulus. Whole lens transmissivity was low indicating an undesirably hazy lens.

COMPARATIVE EXAMPLE 1

A lens shaped sample was fabricated in a manner similar to Working Example 7, except that the silicone acrylamide monomer of the following formula (t1) (made according to Examples 1 and 2 of WO05/078482A1)

[FORMULA 10]

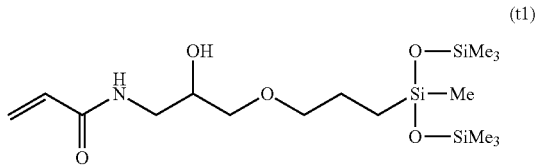

(t1)

was used as the silicone acrylamide monomer in place of the monomer expressed by formula (s2). The whole light transmissivity, water content, elastic modulus, and elongation of the lens shaped sample obtained were as shown in Table 1, and the stress zero time was over 1 second, indicating that the shape recovery properties were not sufficient.

COMPARATIVE EXAMPLE 2

A lens shaped sample was fabricated in a manner similar to working example 7, except that the silicone acrylamide monomer of the following formula (t2) (made according to Examples 5 and 6 of WO05/078482A1)

[FORMULA 11]

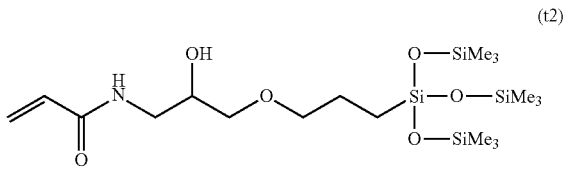

(t2)

was used as the silicone acrylamide monomer in place of the monomer expressed by formula (s2). The whole light transmissivity, water content, elastic modulus, and elongation of the lens shaped sample obtained were as shown in Table 1, and the stress zero time was over 1 second, indicating that the shape recovery properties were not sufficient.

SYNTHESIS EXAMPLE 16

The compound obtained by the same method as synthesis example 6 (20.0 g, 0.072 mol), bis(trimethylsiloxy)methylsilane (16 g, 0.072 mol), toluene (150 mL), and platinum tetra solution (200 µL) were placed in a 500 mL 3-necked flask and a reflex condenser, thermometer, and mechanical stirrer were attached. The reaction was performed at 120° C. for 2 hours. The reaction solution was concentrated in an evaporator, and then purified by distillation under reduced pressure (full vac., 160° C.). The yield was 21.13 g (58.7% yield) and the GC purity was 95.7%.

SYNTHESIS EXAMPLE 17

The compound obtained by synthesis example 16 (20 g, 0.040 mol), triethylamine (8.14 g, 0.040 mol), and ethyl acetate (130 mL) were placed in a 500 mL 3-necked flask and a dropping funnel, thermometer, and mechanical stirrer were attached. Acryloyl chloride (7.28 g, 0.040 mol) and ethyl acetate (100 mL) were placed in the dropping funnel The 3-necked flask was placed in an ice bath containing salt and dropwise addition was started after waiting for the internal temperature to drop to 0° C. While maintaining the internal temperature between −2 and 3° C., dropwise addition was performed over approximately 2 hours and after dropwise addition was completed, the reaction was continued for another hour and then terminated. The solution was then filtered while washing with a small amount of chilled ethyl acetate that had been chilled in a refrigerator. The filtrate was transferred to a separation funnel and 400 mL of hexane was added. The solution was washed two times with water (180 mL), two times with a saturated aqueous solution of sodium hydrogen carbonate (180 mL), and two times with a saturated aqueous solution of sodium chloride (180 mL). Anhydrous sodium sulfate was added to the organic layer and drying was performed overnight. After filtering, this solution was concentrated in an evaporator to obtain crude product. The crude yield was 27.5 g (125% crude yield).

SYNTHESIS EXAMPLE 18

The crude product obtained by synthesis example 17 (26.5 g, 0.048 mol), 3 parts (weight ratio) of methanol (79.5 g) and one half part (weight ratio) of acetic acid (13.3 g) was added for each part of crude product, and then the solution was mixed for 1 hour at 40° C. After reacting, the solution was concentrated in an evaporator. The liquid obtained (48.5 g) was transferred to a separation funnel, and 4 parts of hexane (volumetric ratio) (190 g) were added to one part of liquid. The solution was washed two times each with water (140 mL), a saturated aqueous solution of sodium hydrogen carbonate (140 mL), and a saturated aqueous solution of sodium chloride (170 mL), and then the organic layer was dried overnight using anhydrous sodium sulfate. The solution was concentrated in an evaporator to obtain 16.0 g of crude material. 16.0 g of the crude material was purified in a column. The amount of silica gel used was five times the weight of the crude material (80 g). For the solvent, hexane/ethyl acetate=2/1 was used until impurities were discharged (500 mL), and after confirming that the impurities had been discharged, the target material was eluted using hexane/ethyl acetate=1/2 (750 mL). The range of the fraction containing the target material was confirmed using TLC, and several fractions on both ends of this range were measured by GC, and only fractions where the byproducts were less than 1% were collected. 15 mg of BHT was added and the solution was concentrated in an evaporator. The solution was stirred at 60° C. while reducing the pressure using a vacuum pump for 1 hour in order to remove the remaining solvent, and it was confirmed that a residual solvent peak was not observed using NMR. The yield was 7.5 g (38.3% yield) and the GC purity was 97.7%.

SYNTHESIS EXAMPLE 19

3-Aminopropyltris(trimethylsiloxy)silane (49 g, 0.14 mol) was placed in a 3-necked flask and a reflux condenser, thermometer, and dropping funnel were attached. Glycidol (2,3-epoxy-1-propanol, 3.5 g, 0.05 mol) was added to the dropping funnel, and added by drops over approximately 40 minutes while mixing at 30° C. A GC measurement was performed each hour starting at the time that dropwise addition was completed in order to confirm the progress of the reaction. 20 hours after dropwise addition was completed it was confirmed that the glycidol peak was 1% or less and the reaction was terminated. The solution was concentrated in an evaporator, and then purified by reduced pressure installation (full vac, by 190° C.). The yield was 13.65 g (67.8% yield), and the GC purity was 92.8%.

SYNTHESIS EXAMPLE 20

The compound obtained in synthesis example 19 (12.5 g, 0.03 mol), hexamethyldisilazane (10. g, 0.06 mol), and saccharine (250 mg) were placed in a 3-necked flask and a reflux condenser, and thermometer, mechanical stirrer were attached. The reaction was performed for 2 hours at 100° C. and the reaction was terminated after confirming that the reactants were reduced or exhausted using GC. The reaction solution was concentrated in an evaporator, and then purified by distillation under reduced pressure (full vac, by 170° C.). The yield was 13.3 g (76% yield), and the GC purity was 89.5%.

SYNTHESIS EXAMPLE 21

The compound obtained by synthesis example 20 (13.0 g, 0.023 mol), triethylamine (2.33 g, 0.023 mol), and ethyl acetate (50 mL) were placed in a 1 L 3-necked flask and a dropping funnel, thermometer, and mechanical stirrer were attached. Acryloyl chloride (2.1 g, 0.023 mol) and ethyl acetate (10 mL) were placed in the dropping funnel. The 3-necked flask was placed in an ice bath containing salt and dropwise addition was started after waiting for the internal temperature to drop to 0° C. While maintaining the internal temperature between −2 and 3° C., dropwise addition was performed over approximately 1 hour and after dropwise addition was completed, the reaction was continued for another hour and then terminated. The solution was then filtered while washing with a small amount of chilled ethyl acetate that had been chilled in a refrigerator. The filtrate was transferred to a separation funnel and 60 mL of hexane was added. The solution was washed two times with water (50 mL), two times with a saturated aqueous solution of sodium hydrogen carbonate (50 mL), and two times with a saturated aqueous solution of sodium chloride (50 mL). Anhydrous sodium sulfate was added to the organic layer and drying was performed overnight. After filtering, this solution was concentrated in an evaporator to obtain crude product. The crude yield was 14.2 g and the GC purity was 86.1%.

SYNTHESIS EXAMPLE 22

The crude product obtained by synthesis example 21 (14.0 g), 3 parts (weight ratio) of methanol (42.0 g) and one half part (weight ratio) of acetic acid (7.0 g) was added for each part of crude product, and then the solution was mixed for 4 hour at 40° C. After reacting, the solution was concentrated in an evaporator. The liquid obtained (16.95 g) was transferred to a separation funnel, and 4 parts of hexane (volumetric ratio) (68.0 g) were added to one part of liquid. The solution was washed two times each with water (50 mL), a saturated aqueous solution of sodium hydrogen carbonate (50 mL), and a saturated aqueous solution of sodium chloride (50 mL), and then the organic layer was dried overnight using anhydrous sodium sulfate. The solution was concentrated in an evaporator to obtain 9.95 g of crude material. 9.5 g of the crude material was purified in a column. The amount of silica gel used was five times the weight of the crude material (50 g). For the solvent, hexane/ethyl acetate=2/1 was used until impurities were discharged (300 mL), and after confirming that the impurities had been discharged, the target material was eluted using hexane/ethyl acetate=1/1 (500 mL). The range of the fraction containing the target material was confirmed using TLC, and several fractions on both ends of this range were measured by GC, and only fractions where the byproducts were less than 1% were collected. 4.8 mg of BHT was added and the solution was concentrated in an evaporator. The solution was stirred at 60° C. while reducing the pressure using a vacuum pump for 1 hour in order to remove the remaining solvent, and it was confirmed that a residual solvent peak was not observed using NMR. The yield was 3.14 g (28% yield) and the GC purity was 97.8%.

COMPARATIVE EXAMPLE 3

A lens shaped sample was fabricated in a manner similar to Working Example 7, except that the silicone acrylamide monomer of the following formula (t3)

[FORMULA 12]

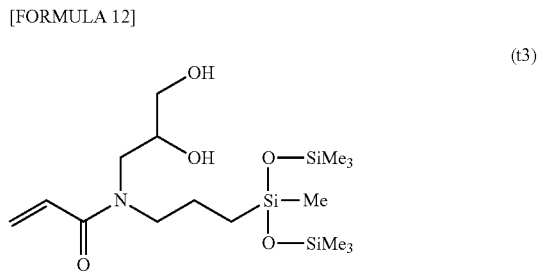

(t3)

obtained by Synthesis Example 16 was used as the silicone acrylamide monomer in place of the monomer expressed by formula (s2). The whole light transmissivity, water content, elastic modulus, and elongation of the lens shaped sample obtained were as shown in Table 1, and the stress zero time was over 1 second, indicating that the shape recovery properties were not sufficient.

COMPARATIVE EXAMPLE 4

A lens shaped sample was fabricated in a manner similar to Working Example 7, except that the following formula (t4), obtained by Synthesis Example 17

[FORMULA 13]

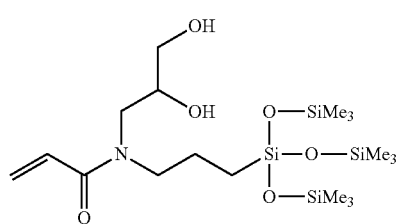
(t4)

was used as the silicone acrylamide monomer in place of the monomer expressed by formula (s2). The whole light transmissivity, water content, elastic modulus, and elongation of the lens shaped sample obtained were as shown in Table 1, and the stress zero time was over 1 second, indicating that the shape recovery properties were not sufficient.

(HEMAA-purchased from Monomer Polymer Dajac Laboratories, Pa.) expressed by the formula (h5)

[FORMULA 23]

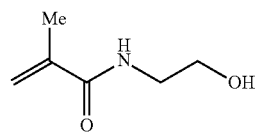
(h5)

was used in place of the monomer expressed by formula (h1) as the non-silicone acrylamide monomer, and except that the silicone monomer and the composition of the silicone monomer, the non-silicone acrylamide and N,N-dimethylacrylamide were changed as shown in Table 2. The appearance, whole light transmissivity, water content, elastic modulus, and elongation of the sample obtained were as shown in Table 2.

TABLE 1

| | Silicone monomer | Center thickness (μM) | Diameter (mm) | Transmissivity (%) | water content (%) | elongation (%) | elastic modulus (psi) | stress zero time (sec) | Advancing contact angle (°) |
|---|---|---|---|---|---|---|---|---|---|
| Working Example 7 | Formula (s2) | 137 | 13.0 | 89.0 | 42.4 | 254 | 95 | 0.89 | 46 |
| Working Example 8 | Formula (s3) | 134 | 12.7 | 91.9 | 38.7 | 197 | 109 | 0.76 | 28 |
| Working Example 9 | Formula (s4) | 135 | 12.9 | 87.5 | 43.5 | 215 | 87 | 0.84 | 98 |
| Working Example 10 | Formula (s2) | 144 | 14.1 | 31.3 | 48.4 | 363 | 61 | 0.74 | 89 |
| Working Example 11 | Formula (s3) | 145 | 14.5 | 52.4 | 49.4 | 354 | 88 | 0.89 | 81 |
| Working Example 12 | Formula (s2) | 146 | 13.9 | 89.9 | 51.4 | 267 | 86 | 0.89 | 59 |
| Working Example 13 | Formula (s3) | 149 | 14.1 | 89.3 | 51.9 | 187 | 114 | 0.92 | 48 |
| Working Example 14 | Formula (s5) | 87 | NA | 6.6 | 44.3 | 238 | 74 | 0.99 | NA |
| Working Example 15 | Formula (s6) | 92 | NA | 7.2 | 43.3 | 293 | 81 | 0.98 | NA |
| Comparative Example 1 | Formula (t1) | 142 | 13.4 | 89.1 | 45.7 | 334 | 85 | 1.07 | 38 |
| Comparative Example 2 | Formula (t2) | 143 | 13.2 | 91.4 | 41.3 | 265 | 145 | 1.24 | 47 |
| Comparative Example 3 | Formula (t3) | 144 | 13.2 | 90.7 | 42.8 | 240 | 438 | 2.65 | 40 |
| Comparative Example 4 | Formula (t4) | 141 | 12.7 | 89.4 | 36.2 | 169 | 705 | 2.95 | 38 |

WORKING EXAMPLE 16 THROUGH 19

A lens sample was fabricated in a manner similar to Working Example 7, except that 2-hydroxyethyl methacrylamide

TABLE 2

| | silicone acrylamide | | non-silicone acrylamide | | N,N-dimethylacrylamide | transmissivity | water content (%) | elastic modulus (psi) | elongation (%) | stress zero time (sec) | Advancing contact angle (degree) |
|---|---|---|---|---|---|---|---|---|---|---|---|
| | formula | (wt %) | formula | (wt %) | (wt %) | (%) | | | | | |
| Working Example 16 | (s2) | 56.06 | (h5) | 7 | 25.27 | 55.1 | 45.7 | 147 | 133 | 0.83 | 61.1 |
| Working Example 17 | (s2) | 56.06 | (h5) | 12 | 20.27 | 84.7 | 41.6 | 165 | 127 | 0.87 | 65.9 |
| Working Example 18 | (s3) | 56.06 | (h5) | 7 | 25.27 | 91.9 | 39.8 | 192 | 162 | 0.88 | 66.7 |
| Working Example 19 | (s3) | 56.06 | (h5) | 12 | 20.27 | 91.1 | 39.2 | 201 | 170 | 0.99 | 77.0 |

WORKING EXAMPLE 20

A monomer mix was prepared in the following molar ratio: the monomer expressed by formula (s2) (32.4 mol %), N,N' dimethyl acrylamide (32.5 mol %), N-(2-hydroxyethyl)acrylamide (32.4 mol %), N,N' methylene bisacrylacrylamide (2.4 mol %), and photoinitiator Irgacure 819 (0.2 mol %). Into the monomer mix (55 weight %), tripropylene glycol methyl ether (TPME, 40 weight %) and polyvinyl pyrrolidone (PVP K90, 5 weight %) were added.

Polymerization of the monomer mix was carried out at 70° C. under dry nitrogen using an LED light source (~420 nm, 4.0 mW/cm$^2$) for 10 minutes, using the DSC procedure described above.

The polymerization rate of the monomer mix was analyzed by photo DSC, which was shown in FIG. 1 as "SA1 RMM". The rate was much faster than that of Comparative Example 5.

WORKING EXAMPLE 21

A monomer mix was prepared in a manner similar to Working Example 20, except that the monomer expressed by the formula (s3) was used as silicone acrylamide monomer in place of the monomer expressed by the formula (s2).

The polymerization rate of the monomer mix was analyzed by photo DSC, which was shown in FIG. 1 as "SA2 RMM". The rate was much faster than that of Comparative Example 5.

COMPARATIVE EXAMPLE 5

A monomer mix was prepared in a manner similar to Working Example 20, except that the silicone methacrylate monomer expressed by the following formula (u1) (made according to Example 29 of WO2008/005229)

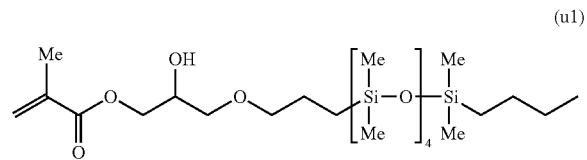

(u1)

was used in place of the silicone acrylamide monomer expressed by the formula (s2), except that 2-hydroxyethyl methacrylate was used in place of 2-hydroxyethylacrylamide, and except that tetraethylene glycol dimethacrylate was used in place of N,N'-methylenebisacrylamide. These monomers were used in the same molar ratio as Working Example 20.

The polymerization rate of the monomer mix was analyzed by photo DSC, which was shown in FIG. 1 as "OH mPDMS RMM".

The invention claimed is:

1. A silicone (meth)acrylamide monomer expressed by the following general formula (a),

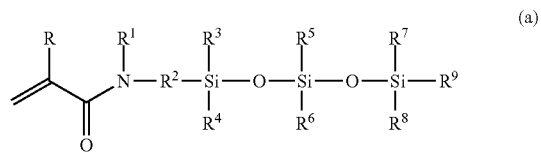

(a)

wherein R represents a hydrogen atom or a methyl group; R$^1$ represents an alkyl or an aryl group with between 1 and 20 carbon atoms which is further substituted with one or more groups selected from the group consisting of hydroxyl groups, acid groups, ester groups, ether groups, thiol groups and combinations thereof; R$^2$ represents a C$_{1-10}$ alkylene group or arylene group that may be substituted with hydroxyl groups, acid groups, ester groups, ether groups, thiol groups and combinations thereof; R$^3$ to R$^9$ independently represent a C$_{1-4}$ alkyl group or an aryl group with between 1 and 20 carbon atoms, either of which may be substituted with fluorine, hydroxyl, acid, ester, ether, thiol and combinations thereof, and n is an integer in a range from 1 to 10.

2. The silicone (meth)acrylamide monomer according to claim 1 wherein R$^1$ represents an alkyl group with between 1 and 5 carbon atoms which is substituted with hydroxyl groups, acid groups, ester groups, ether groups, thiol groups and combinations thereof; R$^2$ represents a C$_{1-5}$ alkylene group that may be substituted with hydroxyl acid, ester, ether, thiol and combinations thereof; R$^3$ to R$^9$ independently represent a C$_{1-4}$ alkyl group and n is an integer in a range from 2 to 6.

3. The silicone (meth)acrylamide monomer according to claim 2, wherein R in general formula (a) represents a hydrogen atom.

4. The silicone (meth)acrylamide monomer according to claim 1, wherein R$^1$ in general formula (a) represents a hydrogen atom or an alkyl group with between 1 and 5 carbon atoms that may have a hydroxyl substitution group.

5. The silicone (meth)acrylamide monomer according to claim 1, wherein R$^2$ represents a propylene group or a structure expressed by the following formula (b)

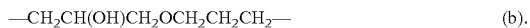

(b).

6. The silicone (meth)acrylamide monomer according to claim 4 or 5, wherein R$^1$ represents a 2,3-dihydroxypropyl group.

7. The silicone (meth)acrylamide monomer according to any one of claims 1 or 2, wherein at least one of R$^3$ and R$^4$, R$^5$ and R$^6$, and R$^7$ and R$^8$ is a methyl group.

8. The silicone (meth)acrylamide monomer according to any one of claim 1 or 2 through 5, wherein R$^9$ is selected from the group consisting of methyl, ethyl and n-butyl group.

9. The silicone (meth)acrylamide monomer according to any one of claim 1 or 2 through 5, where n represents and integer between 1 and 6, and does not have a distribution.

10. A polymer obtained by polymerizing a monomer mixture comprising a silicone (meth)acrylamide monomer according to claims 1 or 2.

11. A polymer according to claim 10, wherein the monomer mixture further comprises N-(mono-hydroxyl substituted C1-C20 alkyl)methacrylamide or N-(mono-hydroxyl substituted C6-C20 aryl)methacrylamide.

12. An ophthalmic lens, comprising a polymer according to claim 10 or 11.

13. A contact lens, comprising a polymer according to claim 10 or 11.

14. The silicone (meth)acrylamide monomer according to any one of claim 1 or 2 through 5, wherein R$^1$ is selected from methyl groups, ethyl groups, n-propyl groups, i-propyl groups, n-butyl groups, s-butyl groups, or t-butyl groups, any of which may be hydroxyl substituted.

15. The silicone (meth)acrylamide monomer according to any one of claims 1 or 2 through 5, wherein R$^2$ is selected from C$_{1-5}$ alkylene groups, which may be unsubstituted or substituted with hydroxyl, ether groups and combinations thereof.

16. The silicone (meth)acrylamide monomer according to any one of claims 1 or 2 through 5, wherein $R^2$ is a $C_3$ alkylene groups, which may be unsubstituted or substituted with hydroxyl, ether groups and combinations thereof.

17. The silicone (meth)acrylamide monomer according to any one of claim 1 or 2 through 5, wherein $R^3$ through $R^9$ are independently selected from alkyl groups with between 1 and 4 carbon atoms.

18. The silicone (meth)acrylamide monomer according to any one of claim 1 or 2 through 5, wherein $R^9$ is an alkyl group with between 1 and 4 carbon atoms which may be unsubstituted or hydroxyl substituted.

* * * * *

UNITED STATES PATENT AND TRADEMARK OFFICE
CERTIFICATE OF CORRECTION

PATENT NO. : 8,415,405 B2
APPLICATION NO. : 13/048469
DATED : April 9, 2013
INVENTOR(S) : Maggio et al.

It is certified that error appears in the above-identified patent and that said Letters Patent is hereby corrected as shown below:

In the Claims

In column 39, claim 1, please correct the chemical formula from:

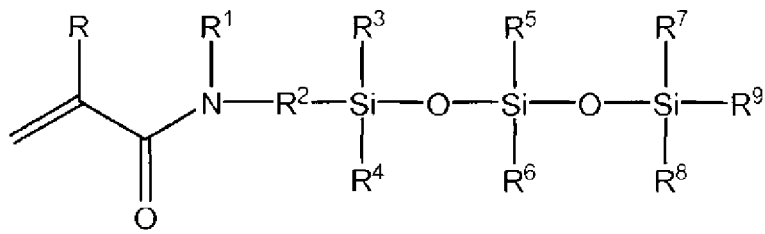

To read:

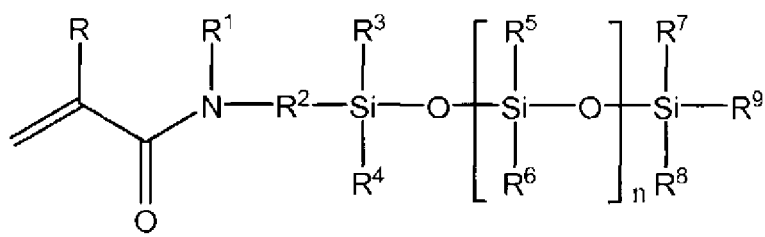

Signed and Sealed this
Twenty-eighth Day of May, 2013

Teresa Stanek Rea
*Acting Director of the United States Patent and Trademark Office*